US008008285B2

(12) United States Patent
Roberts et al.

(10) Patent No.: US 8,008,285 B2
(45) Date of Patent: Aug. 30, 2011

(54) DROXIDOPA AND PHARMACEUTICAL COMPOSITION THEREOF FOR THE TREATMENT OF FIBROMYALGIA

(75) Inventors: Michael J. Roberts, Charlotte, NC (US); Simon Pedder, Fort Mill, SC (US)

(73) Assignee: Chelsea Therapeutics, Inc., Charlotte, NC (US)

( * ) Notice: Subject to any disclaimer, the term of this patent is extended or adjusted under 35 U.S.C. 154(b) by 346 days.

(21) Appl. No.: 12/044,680

(22) Filed: Mar. 7, 2008

(65) Prior Publication Data

US 2008/0221170 A1 Sep. 11, 2008

Related U.S. Application Data

(60) Provisional application No. 60/894,030, filed on Mar. 9, 2007.

(51) Int. Cl.
| A01N 43/40 | (2006.01) |
|---|---|
| A01N 37/44 | (2006.01) |
| A61K 31/44 | (2006.01) |
| A61K 31/195 | (2006.01) |

(52) U.S. Cl. ................. 514/183; 514/351; 514/567
(58) Field of Classification Search .............. 514/183, 514/567, 619
See application file for complete search history.

(56) References Cited

U.S. PATENT DOCUMENTS

| 3,920,728 A | 11/1975 | Hegedüs et al. |
|---|---|---|
| 4,246,428 A | 1/1981 | Ohashi et al. |
| 4,319,046 A | 3/1982 | Vacek |
| 4,330,558 A | 5/1982 | Suzuki et al. |
| 4,421,767 A | 12/1983 | Palfreyman et al. |
| 4,480,109 A | 10/1984 | Ohashi et al. |
| 4,497,826 A | 2/1985 | Narabayashi et al. |
| 4,529,603 A | 7/1985 | Mori et al. |
| 4,562,263 A | 12/1985 | Ohashi et al. |
| 4,647,587 A | 3/1987 | Katsube et al. |
| 4,690,949 A | 9/1987 | Yoshida et al. |
| 4,699,879 A | 10/1987 | Umezawa et al. |
| 4,963,590 A | 10/1990 | Bäckström et al. |
| 5,015,564 A | 5/1991 | Chari |
| 5,015,654 A | 5/1991 | Al-Damluji |
| 5,240,930 A | 8/1993 | Al-Damluji |
| 5,266,596 A | 11/1993 | Yokokawa et al. |
| 5,616,618 A | 4/1997 | Takagi |
| 5,656,669 A | 8/1997 | Nishino |
| 5,739,387 A | 4/1998 | Oda et al. |
| 5,864,041 A | 1/1999 | Oda et al. |
| 6,033,993 A | 3/2000 | Love, Jr. et al. |
| 6,150,412 A | 11/2000 | Pystynen et al. |
| 6,387,936 B1 | 5/2002 | Blanchard-Bregeon et al. |
| 6,512,136 B1 | 1/2003 | Benes et al. |
| 6,610,324 B2 | 8/2003 | Stoll |
| 6,610,690 B2 | 8/2003 | Wong et al. |
| 6,653,325 B2 | 11/2003 | Svensson |
| 6,703,424 B2 | 3/2004 | Levin et al. |
| 6,746,688 B1 | 6/2004 | Kushnir et al. |
| 6,929,801 B2 | 8/2005 | Klose et al. |
| 6,992,110 B2 | 1/2006 | Kranzler et al. |
| 2001/0007856 A1 | 7/2001 | Nishino |
| 2001/0047032 A1 | 11/2001 | Castillo et al. |
| 2002/0177593 A1 | 11/2002 | Ishihara et al. |
| 2003/0181509 A1 | 9/2003 | Hinz |
| 2004/0013620 A1 | 1/2004 | Klose et al. |
| 2004/0152760 A1 | 8/2004 | Castillo et al. |
| 2005/0043408 A1 | 2/2005 | Yeboah et al. |
| 2005/0096387 A1 | 5/2005 | Verheijen et al. |
| 2005/0233010 A1 | 10/2005 | Satow |

FOREIGN PATENT DOCUMENTS

| EP | 0237 929 | | 9/1987 |
|---|---|---|---|
| EP | 0 681 838 | * | 4/1994 |
| EP | 0681838 | * | 11/1995 |
| GB | 2 200 109 A | | 7/1988 |
| WO | WO 2004/032844 A2 | | 4/2004 |
| WO | WO 2004/100929 A1 | | 11/2004 |
| WO | WO 2005/085178 A | | 9/2005 |
| WO | WO 2007/112014 A2 | | 10/2007 |
| WO | WO 2008/003028 A2 | | 1/2008 |

OTHER PUBLICATIONS

Yunus (Semin. Arthritis Rheum. (2007) 36:339-356).*
Mease et. al. (Current pain and headache reports (2008) 12:399-405).*
Lawson (Expert Opinion on Investigational drugs (2002) 11:1437-1445).*
Goldstein (Cardiovascular Drug Reviews (2006) 24:189-203).*
Dadabhoy et. al. (Nature Clinical Practice. Rheumatology (2006) 2:364-372).*
Agmo et al., "A Rat Model of Distractibility: Effect of Drugs Modifying Dopaminergic, Noradrenergic and GABA Ergic Neurotransmission," *Journal of Neural Transmission*, 1997, pp. 11-29, Vo. 104, No. 1. http://www.spingerlink.com/content/n66254211q511485/.
Bennett, et al., "A Peripheral Monoeuropathy in Rat That Produces Disorders of Pain Sensation Like Those Seen in Man," *Pain*, 1988, pp. 81-107, vol. 33, No. 1.
Bradley et al., "Orthostatic Hypotension," *American Family Physician*, 2003, pp. 2393-2398, vol. 68, No. 12.
Brzostowska et al., "Phenylcarbamates of (−)-Eseroline, (−)-N1-Noreseroline and (−)-Physovenol: Selective Inhibitors of Acetyl and, or Butyrylcholinesterase", *Medical Chemistry Research*, 1992, pp. 238-246, vol. 2, No. 4.
Calkins et al., "Relationship Between Chronic Fatigue Syndrome and Neurally Mediated Hypotension," *Cardiology in Review*. (1998), pp. 125-134, vol. 6, No. 3.

(Continued)

*Primary Examiner* — Marcos L Sznaidman
(74) *Attorney, Agent, or Firm* — Womble Carlyle Sandridge & Rice, PLLC

(57) ABSTRACT

The present invention provides methods of treating fibromyalgia or other diseases or conditions causing widespread pain and/or fatigue. In particular, the invention provides pharmaceutical compositions comprising droxidopa alone, or in combination with one or more further active agents, that can be used in the inventive methods. The methods of treatment can comprise treating, preventing, reducing, or eliminating a variety of symptoms recognized as indicative of fibromyalgia, such as chronic pain, allodynia, hyperalgesia, fatigue, sleep disturbance, and depression.

20 Claims, 2 Drawing Sheets

OTHER PUBLICATIONS

Cryan et al., "Norepinephrine-Deficient Mice Lack Responses to Antidepressant Drugs, Including Selective Serotonin Reuptake Inhibitors," *PNAS*, 2004, pp. 8186-8191, vol. 101, No. 21. www.pnas.org/cgi/doi/10.1073/pnas.0401080101.

Edvinsson et al., "Effect of Exogenous Noradrenaline on Local Cerebral Blood Flow After Osmotic Opening of the Blood-Brain Barrier in the Rat," *J. Physiol.*, 1978, pp. 149-156, vol. 274.

Flippen-Anderson et al., Thiaphysovenol Phenylcarbamates: X-ray Structures of Biologically Active and Inactive Anticholinesterase Agents, *Heterocycles*, 1993, pp. 79-86, vol. 36, No. 1.

Greig et al. "Phenserine and Ring C Hetero-Analogues: Drug Candidates for the Treatment of Alzheimer's Disease." *Medicinal Research Reviews*. (1995) vol. 15, No. 1, 3-31.

He et al. "Thiaphysovenine and Carbamate Analogues: A New Class of Potent Inhibitors of Cholinesterases." *Medical Chemistry Research*. (1992) vol. 2, 229-237.

Iida et al., "Effects of L-Threo-3,4-Dihydroxyphenylserine on Orthostatic Hypotension in Hemodialysis Patients," *American Journal of Nephrology*, 2002, pp. 338-346, vol. 22, No. 4, Basel.

Kato et al., "Reversal of the Reserpine-Induced Ptosis by L-Threo-3,4-Dihydroxy-Phenylserine (L-Threo-DOPS), A (−)-Norepinephrine Precursor, and Its Potentiation by Imipramine or Nialamide," *Naunyn-Schmiedeberg's Archies of Pharmacology*, 1986, pp. 243-246, vol. 332, No. 3, Berlin.

Kato et al., "Studies on the Activity of L-Threo-3,4-Dihydroxyphenylserine (L-DOPS) As a Catecholamine Precursor in The Brain, Comparison With Taat of L-DOPA," *Biochemical Pharmacology*, 1987, pp. 3051-3057, vol. 36, No. 18, Great Britain.

Kawabata et al., "The Noradrenaline Precursor L-Threo-3,4-Dihydroxyphenylserine Exhibits Antinociceptive Activity Via Central Alpha-Adrenoceptors in The Mouse," *Br J. Pharmacol*. 1994, pp. 503-508, vol. 111, No. 2, Japan.

Lahiri et al. "Cholinesterase Inhibitors, β-Amyloid Precursor Protein and Amyloid β-Peptides in Alzheimer's Disease." *Acta Neurologica Scandinavia*, (Dec. 2000) vol. 102 (s176), 60-67.

Moldes et al. "The Actions of Dihydroxyphenylalanine and Dihydroxyphenylserine On The Sleep-Wakefulness Cycle of The Rat After Peripheral Decarboxylase Inhibition," *Br J Pharmacol*, 1975, pp. 101-106, vol. 54, No. 1.

Mori et al., "Effects of L-Erythro-3, 4-Dihydroxyphenylserine On Sleep-Wakefulness Patterns and Concentrations of Brain Catecholamines and Serotonin In Rats," *Jpn J Psychiatry Neurol*, 1987, pp. 301-310, vol. 41, No. 2.

Noto et al., "Effects of L-Threo- and Erythro-3,4-Dihydroxyphenylserine on Learning Performance and Concentrations of Brain Noradrenaline and Its Metabolites In Rats," *Pharmacol Biochem Behav.*, 1992, pp. 215-221, Vo. 43, No. 1.

Pei et al. "Total Synthesis of Racemic and Optically Active Compounds Related to Physostigimine and Ring-C Heteroanalogues from 3 [-2'-(Dimethylamino0ethyl]-2,3-dihydro-5-methoxy-1, 3-dimentyl-1H-indol-2-ol." *Helvetica Chimica ACTA*. (1994) vol. 77.

Rowe et al., "Is Neurally Mediated Hypotension an Unrecognised Cause of Chronic Fatigue?" *The Lancet*, 1995, pp. 623-624, vol. 345.

Russell, "Advances in Fibromyalgia: Possible Role for Central Neurochemicals," *Am J Med Sci.*, 1998, pp. 377-384, vol. 315, No. 6.

Schondorf, "Acetylcholinesterase Inhibition in the Treatment of Hypotension," *Journal of Neurology Neurosurgery and Psychiatry*, 2003, pp. 1187, vol. 74, No. 9, www.jnnp.bmjjournals.com.

Singer et al. "Pyridostigmine Treatment Trial in Neurogenic Orthostatic Hypotension", 2006, *Archives of Neurology*. vol. 63, No. 4, pp. 513-518. www.archneur.ama-assn.org.

Takagi et al., "Analgesic Effect of L-Threo-3,4-Dihydroxyphenylserine (L-DOPS) in Patients With Chronic Pain," *Eur Neuropsychopharmacol.*, 1996, pp. 43-47, vol. 6, No. 1, Japan.

Tanaka et al., "The Effects of the Noradrenaline Precursor, L-Threo-3,4-Dihydroxy-Phenylserine, in Children With Orthostatic Intolerance," *Clinical Autonomic Research*, 1996, pp. 189-193, vol. 6.

Tulen et al., "Sleeping With and Without Norepinephrine: Effects of Metoclopramide and D,L-Threo-3,4-Dihydroxyphenylserine on Sleep in Dopamine Beta-Hydroxylase Deficiency," *Sleep*, 1991, pp. 32-38, vol. 14, No. 1. The Netherlands.

Verhagen-Kamerbeek, et al. "Attenuation of Haloperidol-Induced Catalepsy by Noradrenaline and L-Threo-DOPS," *Journal of Neural Transmission. Parkinson's Disease and Dementia Section*, 1993, pp. 17-26, vol. 6. No. 1, Austria.

Yamamoto et al., "Pyridostigmine in Autonomic Failure: Can We Treat Postural Hypotension and Bladder Dysfunction With One Drug?" *Clinical Autonomic Research*, 2006, pp. 296-298, vol. 16, No. 4.

Yoshida et al., "Inhibitory Effects of L-Threo-DOPS on Electroshock Seizure in Mice," *Brain and Nerve*, 1989, pp. 567-573, vol. 41, No. 6, Japan.

Yu et al. "Novel Phenserine-Based-Selective Inhibitors of Butyrylcholinesterase for Alzheimer's Disease." Reprinted with permission from *J. Med. Chem.*, May 20, 1999, 42, 1855-1861.

Yu et al. "Total Syntheses and Anticholinesterase Activities of (3aS)-N (8)-Norphysostigmine, (3aS)-N (8)-Norphenserine, Their Antipodal Isomers, and Other N (8)-Substituted Analogues." *J. Med. Chem.* (1997) vol. 40, 2895-2901.

Zern et al., "Effect of Increased Pancreatic Islet Norepinephrine, Dopamine and Serotonin Concentration on Insulin Secretion in the Golden Hamster," *Diabetologia*, 1980, pp. 341-346, vol. 18, No. 4, Berlin.

www.merck.com, "Orthostatic Hypotension and Syncope," *The Merck Manual of Diagnosis and Therapy*, 1996, Sec. 16, Chapter 200.

Dableh et al., "Antidepressant-like Effects of Neurokinin Receptor Antagonists in the Forced Swim Test in the Rat," *European Journal of Pharmacology*, 2005, pp. 99-105, vol. 507.

Dhir et al., "Effect of Addition of Yohimbine (Alpha-2-Receptor Antagonist) to the Antidepressant Activity of Fluoxetine or Venlafaxine in the Mouse Forced Swim Test," *Pharmacology*, 2007, 239-243, vol. 80.

Goto et al., "Depression in Multiple System Atrophy: A case Report," *Psychiatry and Clinical Neurosciences*, 2000, pp. 507-511, vol. 54.

Joo, et al., "Cerebral Perfusion Abnormality in Narcolepsy with Cateaplexy," *NeuroImage*, 2005, pp. 410-416, vol. 28, No. 2.

Kim et al., "Methylphenidate Increased Regional Cerebral Blood Flow in Subjects with Attention Deficit/Hyperactivity Disorder," *Yonsei Medical Journal*, 2001, pp. 19-29, vol. 42, No. 1.

Lamberti et al., "Antidepressant-like Effects of Endogenous Histamine and of Two Histamine $H_1$ Receptor Agonists in the Mouse Forced Swim Test," *British Journal of Pharmacology*, 1998, pp. 1331-1336, vol. 123.

Lee et al., "Regional Cerebral Blood Flow in Children With Attention Deficit Hyperactivity Disorder: Comparison Before and After Methylphenidate Treatment," *Human Brain Mapping*, 2005, pp. 157-164, vol. 24, No. 3.

Lou et al., "Focal Cerebral Hypoperfusion in Children With Dysphasia and/or Attention Deficit Disorder," *Archives of Neurology*, 1984, pp. 825-829, vol. 41, No. 8.

Porsolt et al., "Behavioural Despair in Mice: A primary Screening Test for antidepressants," *Arch. Int. Pharmacodyn*, 1977, pp. 327-336, vol. 229.

Toda et al., "Parkinson Disease Patient with Fibromyalgia: A Case Report" *Parkinsonism and Related Disorders*, 2007, pp. 312-312, vol. 13.

Goldstein, "L-Dihyroxphenylserine (L-DOPS): A Norepinerphrine Prodrug," *Cardiovascular Drug Reviews*, 2006, pp. 189-203, vol. 24, No. 3-4.

Mathias et al., "L-Threo-dihydroxyphenylserina(L-threo-DOPS; droxidopa) in the management of Neurogenic Orthostatic Hypotension: A Multi-National, Multi-Center, Dose-Ranging Study in Multiple System Atrophy and Pure Autonomic Failure," *Clinical Autonomic Research: Official Journal of the Clinical Autonomic Research Society*, 2001, pp. 235-242, vol. 11, No. 4.

* cited by examiner

DROXIDOPA AND PHARMACEUTICAL COMPOSITION THEREOF FOR THE TREATMENT OF FIBROMYALGIA

CROSS-REFERENCE TO RELATED APPLICATION

The present application claims priority to U.S. Provisional Patent Application No. 60/894,030, filed Mar. 9, 2007, which is incorporated herein by reference in its entirety.

FIELD OF THE INVENTION

The present application is directed to the use of droxidopa, alone or in combination with one or more additional components, for the treatment of Central Sensitivity Syndromes, such as fibromyalgia.

BACKGROUND

Droxidopa is a known synthetic amino acid precursor of norepinephrine that is converted directly to norepinephrine via the action of dopa decarboxylase (DDC). Droxidopa is generally used to treat orthostatic hypotension (OH) and can be categorized as an antiparkinsonian agent; however, multiple pharmacological activities have been observed with droxidopa, including the following: (1) it is directly converted to 1-norepinephrine by the action of the aromatic L-amino acid decarboxylase which is widely distributed in a living body, and thus has an effect of replenishing norepinephrine; (2) it has limited permeability through the blood-brain barrier into the brain; (3) it specifically recovers norepinephrine activated nerve functions which have decreased in the central and peripheral nervous system; and (4) it shows various actions, as norepinephrine, via the adrenaline receptors in various tissues.

Fibromyalgia—also referred to as fibromyalgia syndrome (FMS)—is a chronic pain illness or condition characterized by a generalized heightened perception of sensory stimuli and manifested by widespread aches, pain, and stiffness in muscles, fascia, and joints, as well as soft tissue tenderness. The most common sites of pain include the neck, back, shoulders, pelvic girdle, and hands, but any body part can be affected. Patients with fibromyalgia display abnormalities in pain perception in the form of both allodynia (pain with innocuous stimulation) and hyperalgesia (increased sensitivity to painful stimuli). Other symptoms typically include general fatigue, sleep disturbances, and depression.

Fibromyalgia is characterized by the presence of multiple tender points and a constellation of symptoms. The pain of fibromyalgia is profound, widespread, and chronic and is known to migrate to all parts of the body with varying intensity. Fibromyalgia pain has been described as deep muscular aching, throbbing, twitching, stabbing and shooting pain. Neurological complaints such as numbness, tingling, and burning are often present and add to the discomfort of the patient. Pain severity and stiffness is often worse in the morning, and aggravating factors include cold/humid weather, non-restorative sleep, physical and mental fatigue, excessive physical activity, physical inactivity, anxiety, and stress.

Fatigue associated with fibromyalgia can itself be debilitating, interfering with even the simplest daily activities. At times, fibromyalgia-associated fatigue can leave the patient with a limited ability to function both mentally and physically. Many fibromyalgia patients also have an associated sleep disorder that prevents deep, restful, restorative sleep. Studies have documented specific and distinctive abnormalities in the stage 4 deep sleep of fibromyalgia patients. During sleep, individuals with fibromyalgia are constantly interrupted by bursts of awake-like brain activity limiting the amount of time they spend in deep sleep. Additional symptoms associated with fibromyalgia can include the following: irritable bowel and bladder, headaches and migraines, restless legs syndrome (periodic limb movement disorder), impaired memory and concentration, skin sensitivities and rashes, dry eyes and mouth, anxiety, depression, ringing in the ears, dizziness, hypotension, vision problems, Raynaud's Syndrome, neurological symptoms, and impaired coordination, as well as other symptoms.

Currently there are no known diagnostic tests specific to fibromyalgia. Accordingly, diagnosis generally arises from evaluation of patient histories, self-reported symptoms, physical examination, and an accurate manual "tender point" examination based on the standardized criteria from the American College of Rheumatology (ACR). As defined by ACR guidelines, FMS involves the presence of pain for over three months duration in all four quadrants of the body, as well as along the spine. In addition, pain is elicited by palpation in at least 11 out of 18 "tender points". It is estimated that it takes an average of five years for a fibromyalgia patient to get an accurate diagnosis, and many fibromyalgia symptoms overlap with those of other conditions. Moreover, the presence of comorbidities (such as rheumatoid arthritis or lupus) does not rule out a fibromyalgia diagnosis.

The etiology and pathophysiology of fibromyalgia are unknown; however, it is generally believed to include central nervous system involvement. Most researchers agree fibromyalgia is a disorder of central processing with neuroendocrine/neurotransmitter dysregulation. Fibromyalgia patients often experience pain amplification due to abnormal sensory processing in the central nervous system. Furthermore, studies show multiple physiological abnormalities in fibromyalgia patients, including: increased levels of substance P in the spinal cord; low levels of blood flow to the thalamus region of the brain; HPA axis hypofunction; low levels of serotonin and tryptophan; and abnormalities in cytokine function. Recent studies indicate the possibility of a genetic susceptibility to fibromyalgia.

Treatment of fibromyalgia is often multi-faceted and typically seeks to alleviate the associated symptoms rather than treat the condition itself. Medications, such as analgesics, anti-inflammatories, and muscle relaxants can be beneficial in reducing pain. Antidepressants may also be prescribed. Complementary therapies include: physical therapy, therapeutic massage, myofascial release therapy, water therapy, light aerobics, diet adjustments, acupressure, application of heat or cold, acupuncture, yoga, relaxation exercises, breathing techniques, aromatherapy, cognitive therapy, biofeedback, herbs, nutritional supplements, and osteopathic or chiropractic manipulation. One or more of these may be used.

Despite all of the above approaches for management of fibromyalgia, there remains an ongoing search for effective drug treatment of fibromyalgia. Multiple studies have been performed around a wide variety of compounds, and such studies are further referenced in U.S. Pat. No. 6,610,324, which is incorporated herein by reference. None of the previously evaluated drugs have shown particularly useful for long-term treatment of fibromyalgia beyond symptomatic alleviation, and the need for effective drug treatment of fibromyalgia persists.

SUMMARY OF THE INVENTION

The present invention provides pharmaceutical compositions useful in the treatment of fibromyalgia or other conditions falling under the umbrella of Central Sensitivity Syndrome (CSS). The pharmaceutical compositions generally comprise droxidopa alone or in combination with one or more further pharmaceutically active compounds.

In one aspect, the invention provides a method of treating fibromyalgia. In one embodiment, the method of the invention comprises administering to a subject suffering from fibromyalgia a pharmaceutical composition comprising a therapeutically effective amount of droxidopa.

In certain embodiments, treatment can be indicated in a subject that is suffering from fibromyalgia and exhibiting a symptom known to be indicative of fibromyalgia, such as chronic pain, allodynia, hyperalgesia, fatigue, sleep disturbance, and depression. In such embodiments, the method of treatment can comprise reducing or eliminating the symptom.

In further embodiments, treatment can be indicated in a subject that is suffering from fibromyalgia and is know to have previously exhibited a symptom known to be indicative of fibromyalgia, such as chronic pain, allodynia, hyperalgesia, fatigue, sleep disturbance, and depression. In such embodiments, the method of treatment can comprise preventing re-occurrence of the symptom.

In specific embodiments, the method of the invention comprises treating a patient suffering from fibromyalgia to reduce or eliminate pain associated with the fibromyalgia. Preferably, such fibromyalgia-associated pain is reduced by at least 40%. The effective treatment of fibromyalgia can thus be evidenced by the effective reduction in the fibromyalgia-associated pain.

In other embodiments, the method of the invention comprises treating a patient suffering from fibromyalgia to reduce or eliminate depression associated with the fibromyalgia.

The present invention also provides a variety of combinations of active agents, which combinations can be particularly useful in the treatment of CSS, and particularly fibromyalgia. Thus, the invention provides combinations of droxidopa and one or more further pharmaceutically active compounds, which combinations can be used in methods for treating CSS, particularly fibromyalgia. In certain embodiments, the one or more further pharmaceutically active compounds comprise compounds useful for treatment or prevention of symptoms associated with fibromyalgia. For example, such further pharmaceutically active compounds can comprise antidepressants (such as selective serotonin reuptake inhibitors, tricyclics, serotonin norepinephrine reuptake inhibitors, norepinephrine reuptake inhibitors, and norepinephrine and dopamine reuptake inhibitors), anti-inflammatories, muscle relaxants, antibiotics, mood stabilizers, antipsychotics, serotonin receptor antagonists, serotonin receptor agonists, pain relievers, stimulants, NMDA receptor ligands, s-adenosyl-methionine, zopiclone, chlormezanone, proglumetacin, 5-OH-L-tryptophan, gabapentin, pregabalin, and tamoxefin. In specific embodiments, the invention is directed to a composition comprising droxidopa in combination with one or more antidepressants, such as fluoxetine, paroxetine, citalopram, escitalopram, fluvoxamine, sertraline, amitriptyline, nortriptyline, desipramine, trazodone, venlafaxine, duloxetine, milnacipran, nefopam, bupropion, and combinations thereof.

The invention also comprises methods of treating fibromyalgia comprising administering droxidopa in combination with one or more additional active agents having a complimentary activity to the activity of droxidopa. In one particular embodiment, the invention provides a method of treating fibromyalgia comprising administering a pharmaceutical composition comprising droxidopa and one or more DOPA decarboxylase inhibiting compounds. Preferably, the DOPA decarboxylase inhibiting compounds are selected from the group consisting of benserazide and carbidopa.

In a further embodiment, the invention provides a method of treating fibromyalgia comprising administering a pharmaceutical composition comprising droxidopa and one or more catechol-O-methyltransferase inhibiting compounds. Preferentially, the catechol-O-methyltransferase inhibiting compounds are selected from a specified group of compounds, such as entacapone, tolcapone, and nitecapone.

In another embodiment, the invention provides a method of treating fibromyalgia comprising administering a pharmaceutical composition comprising droxidopa and one or more cholinesterase inhibiting compounds. Preferentially, the cholinesterase inhibiting compounds are selected from a specified group of compounds, such as pyridostigmine, donepezil, rivastigmine, galantamine, tacrine, neostigmine, metrifonate, physostigmine, ambenonium, demarcarium, thiaphysovenine, phenserine, edrophonium, cymserine, and combinations thereof.

In yet another embodiment, the invention provides a method of treating fibromyalgia comprising administering a pharmaceutical composition comprising droxidopa and one or more monoamine oxidase inhibiting compounds. Preferentially, the monoamine oxidase inhibiting compounds are selected from a specified group of compounds, such as selegiline, moclobemide, and lazabemide.

When the droxidopa is combined with one or more additional active agents, the co-administration can be via a variety of methods. For example, the droxidopa and the additional active agent can be in the same pharmaceutical composition. In other embodiments, the droxidopa and the additional active agent can be administered in separate compositions. In such embodiments, the separated compositions can be administered at the same time or within close proximity to one another. Alternatively, the separate compositions can be administered as different times, which may be desirable to optimize the effects of the co-administered active agents.

In another embodiment, the invention is directed to a method of reducing, eliminating, or preventing pain associated with fibromyalgia. The method can particularly comprise administering to a patient diagnosed as suffering from fibromyalgia a pharmaceutical composition comprising a therapeutically effective amount of droxidopa. As above, the method can further comprise administering one or more additional active agents, such as described herein.

The invention also includes kits useful for practicing the methods of the invention, such as a kit comprising a container containing one or more therapeutically effective doses of droxidopa, and an instruction set describing a method for administering a therapeutically effective amount of droxidopa to a subject suffering from a Central Sensitivity Syndrome, such as fibromyalgia.

BRIEF DESCRIPTION OF THE DRAWINGS

Figure 1:
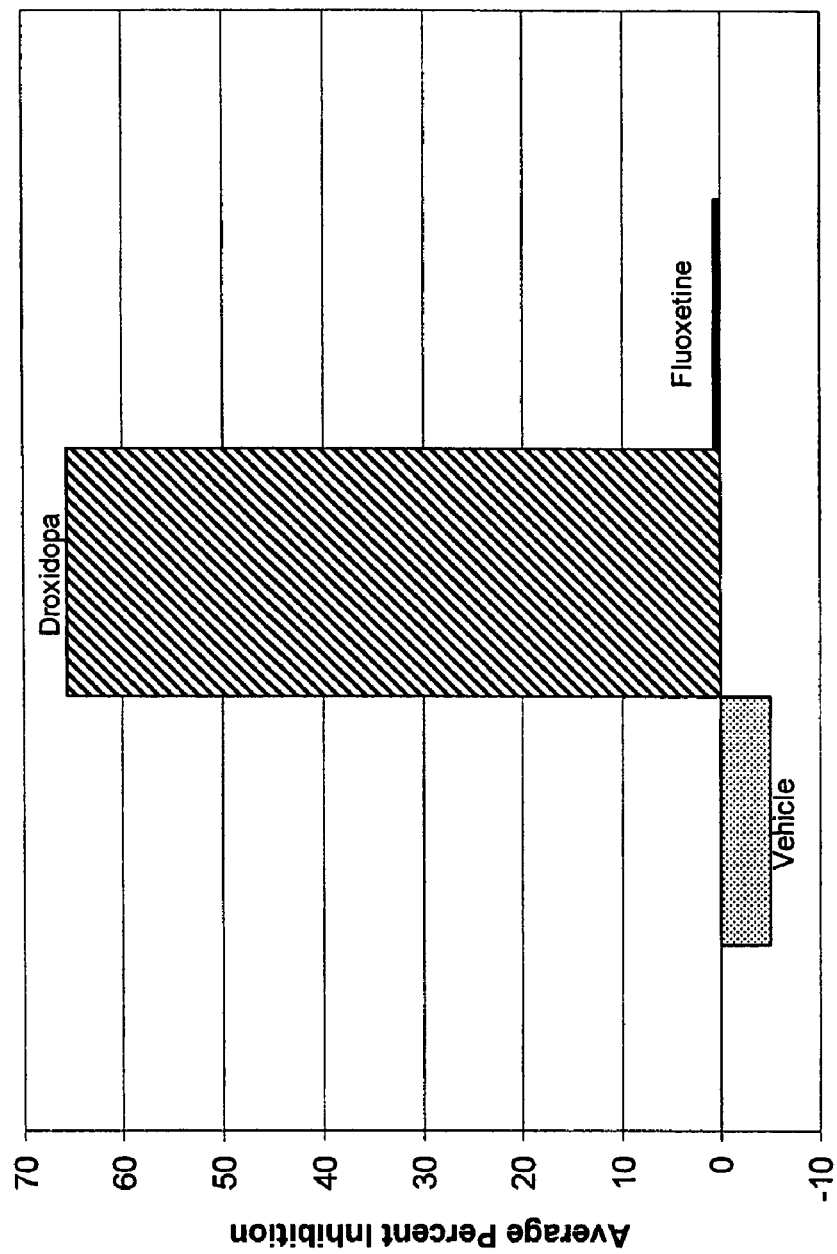
Figure 2:
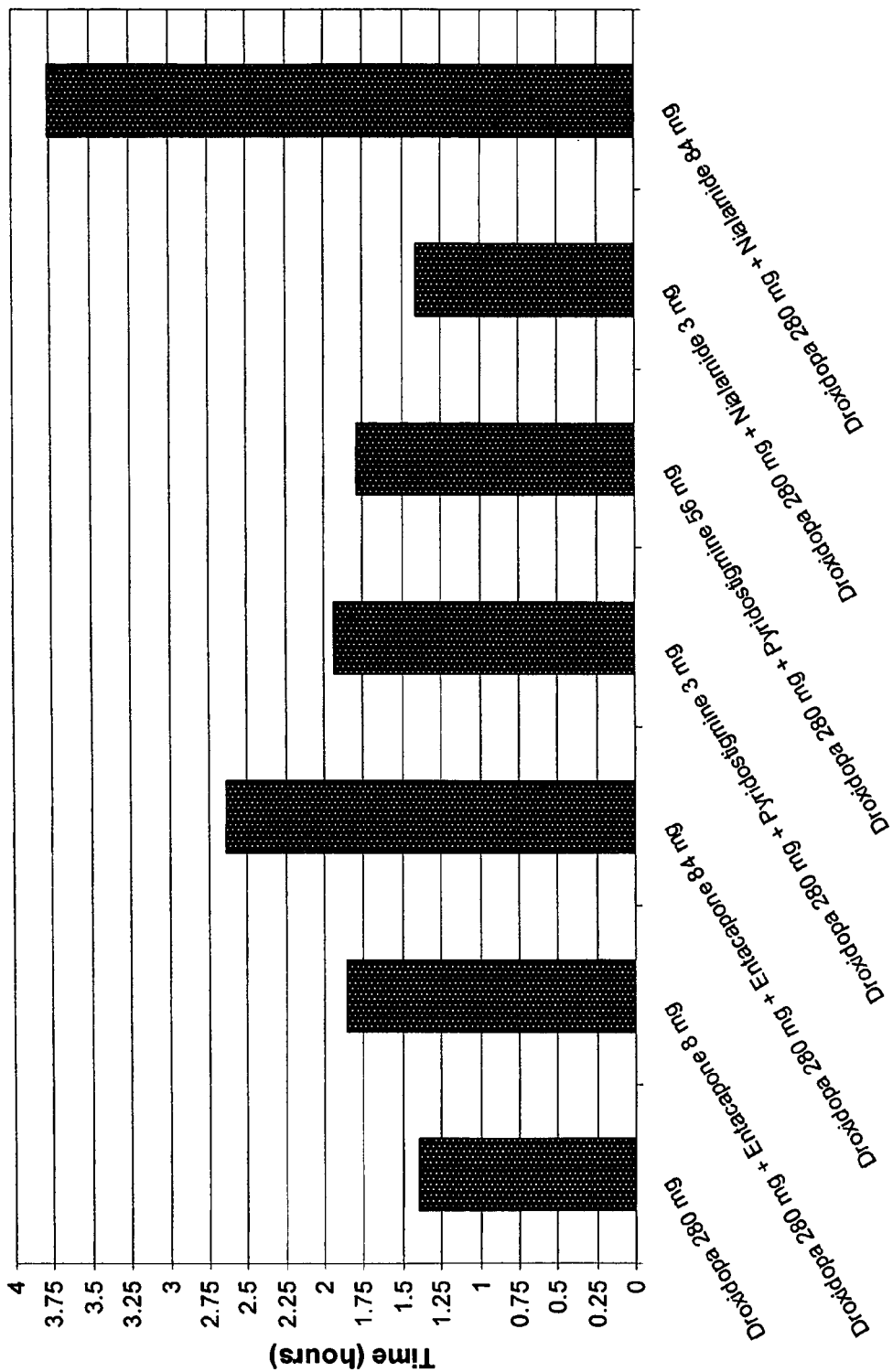

Having thus described the invention in general terms, reference will now be made to the accompanying drawings wherein:

FIG. 1 is a graph illustrating the average percentage inhibition of allodynia in rats following a Chronic Constriction Injury (CCI) and treated with a pharmaceutical vehicle, fluoxetine, or a combination of droxidopa and carbidopa according to one embodiment of the invention; and FIG. 2 is a graphical representation of the half-life of droxidopa in a mammal when administered alone or in combination with various further active agents according to certain embodiments of the invention.

DETAILED DESCRIPTION

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present invention provides pharmaceutical compositions and methods that can be used in the treatment of Central Sensitivity Syndrome (CCS), and particularly fibromyalgia. Treatment can comprise the use of droxidopa as a single active agent. In other embodiments, treatment can comprise the use of droxidopa in combination with one or more further active agents. Such combinations are disclosed in U.S. Patent Application Publication 2008/0015181, which is incorporated herein by reference in its entirety. The specific pharmaceutical composition (or compositions) used in the invention, and the methods of treatment provided by the invention, are further described below.

I. Active Agents

The pharmaceutical compositions of the invention generally comprise droxidopa as an active agent. In certain embodiments, the pharmaceutical compositions can comprise one or more further active agents.

A. Droxidopa

The compositions for use in the methods of the invention generally comprise, as an active agent, threo-3-(3,4-dihydroxyphenyl)serine, which is commonly known as droxidopa and has the structure provided below in Formula (1).

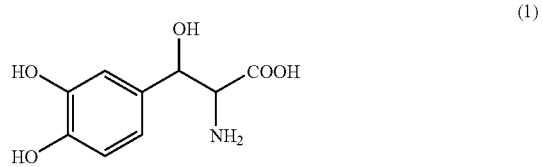

(1)

Droxidopa is also known as threo-β,3-dihydroxy-L-tyrosine, (−)-(2S,3R)-2-amino-3-hydroxy-3-(3,4-dihydroxyphenyl) propionic acid, and threo-dopaserine, as well as the common terms DOPS, threo-DOPS, and L-DOPS. The compound can is optically active and can be provided in various forms, including L-threo-DOPS, D-threo-DOPS, L-erythro-DOPS, and D-erythro-DOPS. The compounds can also exist in the racemic form. The L-threo isomer is generally preferred according to the present invention; however, the invention also encompasses compositions and methods of use incorporating the other forms of droxidopa. Accordingly, as used throughout the present disclosure, the term "droxidopa" is intended to encompass any isolated or purified isomer (e.g., the L-threo isomer), as well as the racemic forms of droxidopa.

Droxidopa useful according to the invention can be prepared by conventional methods, including methods particularly useful for isolating the L-isomer of droxidopa. See, for example, U.S. Pat. No. 3,920,728; U.S. Pat. No. 4,319,040; U.S. Pat. No. 4,480,109; U.S. Pat. No. 4,562,263; U.S. Pat. No. 4,699,879; U.S. Pat. No. 5,739,387; and U.S. Pat. No. 5,864,041, which are incorporated herein by reference.

The present invention also encompasses compositions comprising one or more pharmaceutically acceptable esters, amides, salts, solvates, or prodrugs of droxidopa. In one embodiment, the invention involves use of droxidopa esters that allow for slowed or delayed decarboxylation of droxidopa resulting from hydrolytic or enzymatic degradation of the ester linkage. As would be recognized by one of skill in the art, an ester of droxidopa can be formed by replacing the hydrogen on the carboxylic ester group with any suitable ester-forming group. For example, U.S. Pat. No. 5,288,898, which is incorporated herein by reference, discloses various esters of N-methylphenylserine, including methyl esters, ethyl esters, n-propyl esters, isopropyl esters, n-butyl esters, isobutyl esters, tert-butyl esters, n-pentyl esters, isopentyl esters, n-hexyl esters, and the like, and the present invention encompasses such esters, as well as other esters. Further examples of ester-forming groups that could be used according to the invention are disclosed in U.S. Pat. No. 5,864,041, which is incorporated herein by reference in its entirety.

B. Additional Active Agents

As noted above, in certain embodiments, the compositions for use according to the methods of the invention can comprise one or more active agents in addition to droxidopa. Various preferred active agents that can be combined with droxidopa for treatment of fibromyalgia are described below. Of course, such disclosure should not be viewed as limiting the scope of further active agents that may be combined with droxidopa. Rather, further active compounds, particularly compounds identified as useful for treating fibromyalgia, or for treating or preventing symptoms associated with fibromyalgia, may be used in addition to the compounds specifically disclosed herein.

In one particular embodiment, an active agent used in combination with droxidopa comprises one or more DOPA decarboxylase (DDC) inhibitors. DDC catalyzes the decarboxylation of levodopa (L-DOPA or 3,4-dihydroxy-L-phenylalanine) and 5-hydroxytryptophan (5-HTP) to yield dopamine and serotonin, respectively. Similarly, DDC catalyzes the conversion of droxidopa to norepinephrine. DDC inhibitors prevent the above-noted conversions and are useful in combination with precursor drugs (such as droxidopa) to focus conversion within the central nervous system and thus increase the concentration of droxidopa in the CNS.

Any compound typically recognized as inhibiting or decreasing the activity of DDC can be used according to the present invention. Non-limiting examples of DDC inhibitors useful according to the invention comprise benserazide, carbidopa, difluoromethyldopa, α-methyldopa, and combinations thereof.

In further embodiments, an active agent used in combination with droxidopa comprises one or more compounds that at least partially inhibit the function of catechol-O-methyltransferase (such compounds being generally referred to as "COMT inhibitors"). Catechol-O-methyltransferase catalyzes the transfer of the methyl group from S-adenosyl-L-methionine to various catechol compounds (e.g., catecholamines), including dopamine, epinephrine, norepinephrine, and droxidopa. The COMT enzyme is important in the extraneuronal inactivation of catecholamines and drugs with catechol structures, and is generally one of the most important enzymes involved in the metabolism of catecholamines and their metabolites. It is present in most tissues, including the peripheral and the central nervous system.

Inhibitors of COMT slow metabolism and elimination of catechol compounds by increasing their half-life. Accordingly, COMT inhibitors can function to increase levels of naturally occurring catechol compounds, as well as alter the pharmacokinetics of administered catechol compounds (such as L-β-3,4-dihydroxyphenylalanine (L-DOPA), an immediate precursor of dopamine, generally used for symptomatic treatment of Parkinson's disease). Inhibitors of COMT can act peripherally (such as the compound entacapone), while others (such as tolcapone) are capable of crossing the blood-brain barrier and thus acting centrally and peripherally.

Any compound generally recognized as being a COMT inhibitor can be used as an additional active agent according to the invention. Non-limiting examples of COMT inhibitors useful in combination with droxidopa for treatment of fibromyalgia according to the invention include the following: [(E)-2-cyano-N,N-diethyl-3-(3,4-dihydroxy-5-nitrophenyl) propenamide], also called entacapone (COMTAN®); 4-dihydroxy-4'-methyl-5-nitrobenzophenone, also called tolcapone (TASMAR®); and 3-(3,4-dihydroxy-5-nitrophenyl)methylene-2,4-pentanedione, also called nitecapone. In addition to the above examples, U.S. Pat. No. 6,512,136 (the disclosure of which is incorporated herein by reference) describes various substituted 2-phenyl-1-(3,4-dihydroxy-5-nitrophenyl)-1-ethanone compounds that may also be useful as COMT inhibitors according to the present invention. Likewise, U.S. Pat. No. 4,963,590; GB 2 200 109; U.S. Pat. No. 6,150,412; and EP 237 929, each describes groups of COMT inhibiting compounds that could be useful according to the present invention, and the disclosure of each of the above-noted documents is incorporated herein by reference.

According to another embodiment of the invention, an active agent used in combination with droxidopa comprises one or more compounds that at least partially inhibit the function of cholinesterase. Such cholinesterase inhibiting compounds may also be referred to as anticholinesterase compounds. Cholinesterase inhibiting compounds can be reversible or non-reversible. The present invention preferably encompasses any compounds that may be considered reversible cholinesterase inhibitors (either competitive or non-competitive inhibitors). Non-reversible cholinesterase inhibitors generally find use as pesticides (such as diazinon and Sevin) and chemical weapons (such as tabin and sarin) and are not preferred according to the present invention.

Cholinesterase inhibitors are understood to include compounds that increase levels of acetylcholine (or a cholinergic agonist), generally by reducing or preventing the activity of chemicals involved in the breakdown of acetylcholine, such as acetylcholinesterase. Cholinesterase inhibitors may also include compounds having other mechanisms of action, such as stimulating release of acetylcholine, enhancing response of acetylcholine receptors, or potentiating gonadotropin releasing hormone (GNRH)-induced growth hormone release. Moreover, cholinesterase inhibitors may act by enhancing ganglionic transmission.

Any compound generally recognized as being a cholinesterase inhibitor (or an anticholinesterase compound) may be useful according to the present invention. Non-limiting examples of cholinesterase inhibitors useful in combination with droxidopa for preparing compositions according to the invention include the following: 3-dimethylcarbamoyloxy-1-methylpyridinium, also called pyridostigmine (MESTINON® or Regonol); (±)-2,3-dihydro-5,6-dimethoxy-2-[[1-(phenylmethyl)-4-piperidinyl]methyl]-1H-inden-1-one, also called donepezil (ARICEPT®); (S)—N-ethyl-3-((1-dimethyl-amino)ethyl)-N-methylphenyl-carbamate, also called rivastigmine (Exelon); (4aS,6R,8aS)-4-a,5,9,10,11,12-hexahydro-3-methoxy-11-methyl-6H-benzofuro[3a,3,2ef] [2]benzazepin-6-ol, also called galantamine (REMINYL® or RAZADYNE®); 9-amino-1,2,3,4-tetrahydroacridine, also called tacrine (COGNEX®); (m-hydroxyphenyl) trimethylammonium methylsulfate dimethylcarbamate, also called neostigmine; 1-hydroxy-2,2,2-trichloroethylphosphonic acid dimethyl ester, also called metrifonate or trichlorofon; 1,2,3,3A,8,8A-hexahydro-1,3a,8-trimethylpyrrolo-[2,3-b]-indole-5-ol methylcarbamate ester, also called physostigmine; [Oxalylbis(iminoethylene)]-bis-[(o-chlorobenzyl)diethylammonium]dichloride, also called ambenonium (MYTELASE®); ethyl (m-hydroxyphenyl)dimethylammonium, also called edrophonium (ENLON®); demarcarium; thiaphysovenine; phenserine; and cymserine.

More generally, compounds useful as cholinesterase inhibitors according to the invention can comprise carbamate compounds, particularly phenylcarbamates, oganophosphate compounds, piperidines, and phenanthrine derivatives. The invention further comprises cholinesterase inhibitors that are carbamoyl esters, as disclosed in U.S. Published Patent Application No. 2005/0096387, which is incorporated herein by reference.

The above groups of compounds, and specific compounds, are provided to exemplify the types of cholinesterase inhibitors that are useful according to the invention and should not be viewed as limiting the scope of the invention. In fact, the invention can incorporate various further cholinesterase inhibitors, including compounds described in the following documents, the disclosures of which are incorporated herein by reference: Brzostowska, Malgorzata, et al. "Phenylcarbamates of (−)-Eseroline, (−)—N1-Noreseroline and (−)-Physovenol: Selective Inhibitors of Acetyl and, or Butyrylcholinesterase." *Medical Chemistry Research*. (1992) Vol. 2, 238-246; Flippen-Anderson, Judith L., et al. "Thiaphysovenol Phenylcarbamates: X-ray Structures of Biologically Active and Inactive Anticholinesterase Agents." *Heterocycles*. (1993) Vol. 36, No. 1; Greig, Nigel H., et al. "Phenserine and Ring C Hetero-Analogues: Drug Candidates for the Treatment of Alzheimer's Disease." *Medicinal Research Reviews*. (1995) Vol. 15, No. 1, 3-31; He, Xiao-shu, et al. "Thiaphysovenine and Carbamate Analogues: A New Class of Potent Inhibitors of Cholinesterases." *Medical Chemistry Research*. (1992) Vol. 2, 229-237; Lahiri, D. K., et al. "Cholinesterase Inhibitors, β-Amyloid Precursor Protein and Amyloid β-Peptides in Alzheimer's Disease." *Acta Neurologica Scandinavia*. (December 2000) Vol. 102 (s176), 60-67; Pei, Xue-Feng, et al. "Total Synthesis of Racemic and Optically Active Compounds Related to Physostigimine and Ring-C Heteroanalogues from 3-[-2'-(Dimethylamino0ethyl]-2,3-dihydro-5-methoxy-1,3-dimentyl-1H-indol-2-ol." *Helvetica Chimica ACTA*. (1994) Vol. 77; Yu, Qian-sheng, et al. "Total Syntheses and Anticholinesterase Activities of (3aS)—N (8)-Norphysostigmine, (3aS)—N (8)-Norphenserine, Their Antipodal Isomers, and Other N (8)-Substituted Analogues." *J. Med. Chem*. (1997) Vol. 40, 2895-2901; and Yu, Q. S., et al. "Novel Phenserine-Based-Selective Inhibitors of Butyrylcholinesterase for Alzheimer's Disease." Reprinted with permission from *J. Med. Chem*., May 20, 1999, 42, 1855-1861.

According to yet another embodiment of the invention, an active agent used in combination with droxidopa comprises one or more compounds that at least partially inhibit the function of monoamine oxidase. Monoamine oxidase inhibitors (MAOIs) comprise a class of compounds understood to act by inhibiting the activity of monoamine oxidase, an enzyme generally found in the brain and liver of the human body, which functions to break down monoamine compounds, typically through deamination.

There are two isoforms of monoamine oxidase inhibitors, MAO-A and MAO-B. The MAO-A isoform preferentially deaminates monoamines typically occurring as neurotransmitters (e.g., serotonin, melatonin, epinephrine, norepinephrine, and dopamine). Thus, MAOIs have been historically prescribed as antidepressants and for treatment of other social disorders, such as agoraphobia and social anxiety. The MAO-B isoform preferentially deaminates phenylethylamine and trace amines. Dopamine is equally deaminated by both isoforms. MAOIs may by reversible or non-reversible and may be selective for a specific isoform. For example, the MAOI moclobemide (also known as Manerix or Aurorix) is known to be approximately three times more selective for MAO-A than MAO-B.

Any compound generally recognized as being an MAOI may be useful according to the present invention. Non-limiting examples of MAOIs useful in combination with droxidopa for preparing compositions according to the invention include the following: isocarboxazid (MARPLAN®); moclobemide (Aurorix, Manerix, or Moclodura); phenelzine (NARDIL®); tranylcypromine (PARNATE®); selegiline (ELDEPRYL®, EMSAM®, or 1-deprenyl); lazabemide; nialamide; iproniazid (marsilid, iprozid, ipronid, rivivol, or propilniazida); iproclozide; toloxatone; harmala; brofaromine (Consonar); benmoxin (Neuralex); and certain tryptamines, such as 5-MeO-DMT (5-Methoxy-N,N-dimethyltryptamine) or 5-MeO-AMT (5-methoxy-α-methyltryptamine).

In specific embodiments, active agents used in combination with droxidopa comprise one or more compounds useful for treating fibromyalgia or for reducing or preventing occurrence of symptoms associated with fibromyalgia. As previously discussed, fibromyalgia manifests itself by a variety of symptoms including pain of the joints, muscles, and fascia, fatigue, sleep disturbance, and depression. Accordingly, the additional active agents of the invention can comprise compounds useful for treating, reducing, or preventing any of the above-noted symptoms that present with fibromyalgia.

In certain embodiments, the present invention provides a method for treating fibromyalgia comprising administering a combination of droxidopa and one or more antidepressants (in addition to MAOIs already noted above). Antidepressants useful according to the invention comprise selective serotonin reuptake inhibitors (SSRIs), tricyclics, serotonin norepinephrine reuptake inhibitors (5-HT-NE dual reuptake inhibitors), norepinephrine reuptake inhibitors (NRIs), and norepinephrine and dopamine reuptake inhibitors (NDRIs). Non-limiting examples of specific antidepressants useful according to the invention comprise fluoxetine, paroxetine, citalopram, escitalopram, fluvoxamine, sertraline, amitriptyline, nortriptyline, desipramine, trazodone, venlafaxine, duloxetine, milnacipran, nefopam (including (+)-nefopam), and bupropion. For example, U.S. Patent Application Publication No. 2006/0019940, which is incorporated herein by reference in its entirety, discloses benzoxazocine compounds useful as noradrenaline and serotonin reuptake inhibitors, and such compounds are useful according to the present invention.

In further embodiments, the present invention provides a method for treating fibromyalgia comprising administering a combination of droxidopa and one or more anti-inflammatories. Anti-inflammatories useful according to the invention comprise steroidal anti-inflammatories and non-steroidal anti-inflammatory drugs (NSAIDs). Non-limiting examples of specific anti-inflammatories useful according to the invention comprise prednisone, cortisone, dexamethasone, methylprednisone, ibuprofen, ketoprofen, aspirin, naproxen, and Cox-II inhibitors, such as celebrex.

In additional embodiments, the present invention provides a method for treating fibromyalgia comprising administering a combination of droxidopa and one or more muscle relaxants. Muscle relaxants useful according to the invention comprise both benzodiazepines and non-benzodiazepines. Non-limiting examples of specific muscle relaxants useful according to the invention comprise diazepam, alprazolam, lorazepam, triazolam, baclofen, carisoprodol, chlorzoxazone, cyclobenzaprine, dantrolene, metaxalone, orphenadrine, pancurion, and tizanidine.

The above compounds and classes of compounds are only examples of the types of active agents that can be used in combination with droxidopa for the treatment of fibromyalgia and are not intended to be limiting of the invention. Rather, various further active agents can be combined with droxidopa according to the invention. Moreover, it is possible according to the invention to combine two or more additional active agents with droxidopa for the treatment of fibromyalgia. Non-limiting examples of further active agents that can be combined with droxidopa include: antibiotics (such as those specific for lyme disease); mood stabilizers (such as lithium, olanzipine, verapamil, quetiapine, lamotrigine, carbamazepine, valproate, oxcarbazepine, risperidone, aripiprazole, and ziprasidone); antipsychotics (such as haloperidol and other butyrophenones, chlorpromazine, fluphenazine, perphenazine, prochlorperazine, and other phenothiazines, and clozapine); serotonin receptor antagonists (5-HT2 and 5-HT3 antagonists) (such as ondansetron, tropisetron, katenserin, methysergide, cyproheptadine, and pizotifen); serotonin receptor agonists (5-HT1A receptor agonists) (such as buspirone); pain relievers (such as acetaminophen, flupirtine, and tramadol); stimulants (such as caffeine or modafinil); NMDA (glutamate) receptor ligands (such as ketamine); s-adenosylmethionine; zopiclone; chlormezanone; proglumetacin; 5-OH-L-tryptophan; gabapentin, pregabalin, and tamoxefin. Although the above compounds are described in terms of classes of compounds and specific compounds, it is understood that there is substantial overlap between certain classes of compounds (such as between mood stabilizers, antipsychotics, antidepressants, and serotonin receptor antagonists). Thus, specific compounds exemplifying a specific class of compounds may also properly be identified with one or more further classes of compounds. Accordingly, the above classifications should not be viewed as limiting the scope of the types of compounds useful in combination with droxidopa for treating fibromyalgia.

II. Methods of Treatment

The present invention, in a specific embodiment, provides a method for the treatment of fibromyalgia. In further embodiments, the invention more generally provides methods of treating conditions having the pathophysiology of central sensitization, typically causing widespread pain and/or fatigue. Such conditions may be grouped into the category of Central Sensitivity Syndromes (CSS) and include disorders such as fibromyalgia, chronic myofascial pain, chronic fatigue syndrome, restless leg syndrome, and irritable bowel syndrome.

Throughout the present specification, the method of treatment of the invention may be referenced in terms of treatment of fibromyalgia. While treatment of fibromyalgia is a preferred embodiment of the invention, disclosure in terms thereof is not intended to limit the scope of the invention. Rather, as further described below, the present invention can provide methods of treating a variety of diseases or conditions characterized by widespread pain and/or fatigue, particularly those conditions typically recognized under the CSS category.

The methods of the invention generally comprise administering droxidopa to a patient suffering from a condition of central sensitization or a condition generally causing widespread pain and/or fatigue. In a specific embodiment, the invention comprises administering droxidopa to a patient exhibiting symptoms of, or having been diagnosed as suffering from, fibromyalgia. In further embodiments, the invention comprises administering droxidopa to a patient suffering from one or more further conditions included in the category of Central Sensitivity Syndromes. Accordingly, the present invention can be described as providing methods for treating a condition categorized as a Central Sensitivity Syndrome. In certain embodiments, the invention provides methods of treating fibromyalgia. In other embodiments, the invention can be described as providing methods for treating, reducing, or preventing a symptom associated with fibromyalgia. In particular, the invention provides methods for treating, reducing, or preventing chronic pain, allodynia, hyperalgesia, fatigue, sleep disturbance, and depression associated with fibromyalgia or another condition categorized as CSS.

Thus, in specific embodiments, the inventive method can comprise treating a patient suffering from fibromyalgia. In particular, the patient can be a patient suffering from a symptom, such as described above, typically associated with fibromyalgia, and the treatment can comprise reducing or eliminating the symptom. Likewise, the patient can be a patient that has previously suffered from a symptom of fibromyalgia, and the treatment can comprise preventing re-occurrence of the symptom or reducing the severity of the symptom upon re-occurrence.

Although the exact underlying cause of fibromyalgia is not completely understood, most researchers agree fibromyalgia involves a processing disorder in the central nervous system including neuroendocrine/neurotransmitter dysregulation. In particular, fibromyalgia has been associated with reduced levels of the neurotransmitters serotonin and norepinephrine, and avenues for increasing neurotransmitter levels within the brain can be effective in treating fibromyalgia. Because serotonin and norepinephrine are thought to be key mediators of descending pain pathways, increasing levels of these neurotransmitters can particularly be useful for reducing pain associated with fibromyalgia. Interventions for fibromyalgia thus have included neurotransmitter reuptake inhibitors; however, many reuptake inhibitors also cause undesirable side effects (e.g., weight changes, sleep disruption, and sexual dysfunction).

Droxidopa is converted to norepinephrine by the action of the aromatic L-amino acid decarboxylase DDC. Droxidopa is believed to be useful for treating conditions of central sensitization, and particularly fibromyalgia, because of its ability to increase norepinephrine levels via the noted conversion process. Since fibromyalgia (and other conditions categorized under the heading of CSS) are linked to reduced norepinephrine levels, treatments that increase the available amount of norepinephrine, particularly in the CNS, are beneficial for treating such conditions. For example, some published research indicates a possible link between autonomic dysfunction (i.e., orthostatic hypotension) and fibromyalgia. Such research confirms the relationship between reduced norepinephrine levels and fibromyalgia, and increasing norepinephrine levels would thus be indicated for treating fibromyalgia. See Lowe, P., (1998) *Cardiol. Rev.* 6(3); 125-134, and Lowe, P. (1995), *Lancet* 345(8950): 623-624.

As previously noted, fibromyalgia is a chronic pain condition characterized by a generalized heightened perception of sensory stimuli and manifested by widespread aches, pain, and stiffness in muscles, fascia, and joints, as well as soft tissue tenderness. Patients with fibromyalgia display abnormalities in pain perception in the form of both allodynia (pain with innocuous stimulation) and hyperalgesia (increased sensitivity to painful stimuli). Thus, there is a clear connection between pain alleviation and effective fibromyalgia treatment, and this connection is well documented in the literature.

A 1998 study by I. J. Russell (*Am. J. Med. Sci.*, 315(6): 377-384) noted that the term allodynia is properly associated with fibromyalgia because people with fibromyalgia experience pain from pressure stimuli that are not normally painful. Thus, Russell determined that the nociceptive neurotransmitters of animal studies are relevant to the human model of chronic, widespread pain that is common with fibromyalgia. The association between pain and fibromyalgia and the efficacy for treatment of fibromyalgia as evidenced by effective treatment of chronic pain is further supported in the literature. A 2005 study by Bomholt et al. (*Brain Res.*, 1044(2): 216-226) illustrated that chronic pain conditions, such as fibromyalgia, are associated with profound hypothalamo-pituitary-adrenal (HPA) axis dysfunction which can exacerbate symptoms of chronic pain. Another 2005 study by Pedersen et al. (*Psychopharmacology (Berl)*, 182(4): 551-561) determined that anti-nociception is selectively enhanced by parallel inhibition of multiple subtypes of monoamine transporters in rat models of persistent and neuropathic pain. A 2002 study by Gracety et al. (*Arthritis & Rheumatism*, 46(5): 1333-1343) used functional magnetic resonance imaging (fMRI) to provide evidence that fibromyalgia is characterized by cortical and subcortical augmentation of pain processing in the human brain. A 1988 study by Bennett, G. J. and Xie, Y. K. (*Pain*, 33(1): 87-107) indicated that a rat model of peripheral mononeuropathy produced through chronic constrictive injury (CCI) was an effective model of pain sensation disorders like those experienced by humans. Example 1 below uses such a model to illustrate the effectiveness of the invention for treating fibromyalgia through reduction of chronic pain.

The invention is thus particularly characterized by the ability to treat fibromyalgia through reducing or eliminating pain associated with the fibromyalgia. Such pain can be chronic pain, allodynia, or hyperalgesia, all of which are commonly associated with fibromyalgia and are recognized as clear indicators that a patient is suffering from fibromyalgia. In specific embodiments, the methods of the present invention are useful for reducing pain by at least about 30%. Such reduction in pain can be determined by objective testing, such as measuring a patient's response palpation of known pain sites. Likewise, pain reduction can be evaluated as a subjective report from the patient describing the patient's overall pain level in light of the treatment. Preferably, the methods of the invention are useful for reducing pain by at least about 40%, at least about 50%, at least about 60%, at least about 70%, at least about 80%, or at least about 90%. In specific embodiments, pain can be completely eliminated by treatment according to the invention.

In other specific embodiments, the methods of the invention are particularly useful for reducing or eliminating depression associated with fibromyalgia. It is readily recognized that depression and fibromyalgia often coincide. The chronic pain of fibromyalgia, as well as the dearth of effective treatments, can often lead to depression. There may also be a common underlying cause, however, in the link between neurotransmitter levels and depression and fibromyalgia. Thus, it has been found according to the present invention that treatment of fibromyalgia can be evidenced by the effective reduction or elimination of the depressive state often associated with fibromyalgia. A reduction in depression can be indicated as a self-reported improvement by the patient. Further, reduced depression (and thus effective treatment of fibromyalgia) can also be indicated by objective evaluation of a previously depressed subject and noting certain indicators of reduced depression, such as increased activity, increased interest in various stimuli, and the like.

The methods of treatment provided by the present invention comprise administering, to a subject suffering from fibromyalgia, droxidopa or droxidopa in combination with one or more further active agents, as described herein. In certain embodiments, the one or more further active agents provide a conserving effect on the droxidopa. In further embodiments, the one or more further active agents provide a complimentary effect to the action of the droxidopa, preferably treating or reducing one or more of the symptoms associated with fibromyalgia, such as pain, depression, fatigue, hypotension, or sleep disturbance.

In particular embodiments, droxidopa is combined with one or more DDC inhibitors. Such a combination is particularly beneficial for focusing the effect of the droxidopa in increasing norepinephrine levels. Many DDC inhibitors, such as benserazide and carbidopa, do not enter the central nervous system. Rather, they remain within the periphery where they prevent decarboxylation of compounds (such as levodopa or droxidopa) into the active metabolites (such as norepinephrine). Thus, when a non-CNS DDC inhibitor is administered in combination with droxidopa, the DDC inhibitor prevents decarboxylation of the droxidopa in the periphery and therefore allows more droxidopa to enter the CNS intact. Once within the CNS (and thus segregated from the DDC inhibitor), the droxidopa can be converted to norepinephrine. Accordingly, the combination of a DDC inhibitor with droxidopa can increase the effective ability of the droxidopa to provide norepinephrine within the CNS and thereby reduce the dose of droxidopa necessary to be effective in treating fibromyalgia.

As previously noted, catechol-O-methyltransferase is directly involved in the metabolism of catecholamines, including dopamine, epinephrine, norepinephrine, and droxidopa. Accordingly, by providing droxidopa in combination with a COMT inhibitor, the ability of the droxidopa to affect fibromyalgia is conserved. Specifically, by inhibiting the action of COMT, the COMT inhibiting compound slows or delays the metabolism of droxidopa (as well as norepinephrine itself). This influences the overall plasma concentration of the droxidopa by increasing both the peak plasma concentration ($C_{max}$) and the half-life of the administered droxidopa. This is particularly beneficial in that it allows for reduced dosages of droxidopa without limiting effective treatment of fibromyalgia. Further, the combination of the COMT inhibitor with droxidopa may be effective for increasing the duration of the droxidopa activity (i.e., increasing the duration of norepinephrine activity), which may allow for a reduction in dosing frequency of the droxidopa.

The combination of droxidopa with an MAOI has a similar effect of conserving bodily norepinephrine levels. In particular embodiments, the MAOI inhibits the action of monoamine oxidase in breaking down norepinephrine, including that formed from the conversion of droxidopa. Accordingly, droxidopa plasma concentrations are positively influenced as the half-life of the droxidopa is increase. This is again particularly beneficial in allowing for reduced droxidopa dosages without limiting effective treatment of fibromyalgia. Moreover, the combination of the MAOI with droxidopa is also effective for increasing droxidopa activity duration, which again may allow for a reduction in dosing frequency of the droxidopa.

In certain embodiments, the combination of droxidopa with cholinesterase inhibitors is particularly effective arising from synergistic properties. As previously noted, certain cholinesterase inhibitors (such as pyridostigmine) have been found to enhance ganglionic transmission, thereby directly affecting fibromyalgia and providing some degree of treatment for fibromyalgia and its associated symptom. The synergistic effect of the cholinesterase inhibitor with droxidopa can therefore be envisioned. For example, in a specific embodiment, pyridostigmine could be combined with droxidopa, the pyridostigmine enhancing ganglionic neurotransmission while the droxidopa acts to load the postganglionic neuron with norepinephrine.

The combination of droxidopa with the further active agents is also particularly useful in the treatment of fibromyalgia. For example, combining droxidopa with one or more antidepressants can lead to a synergistic effect. Moreover, treatments that affect neurotransmitter levels are known to require a "build-up" phase of one to three weeks to reach maximum effectiveness. Thus, combining droxidopa with one or more further active agents that can provide immediate relief to symptoms associated with fibromyalgia, such as inflammation or sleep disorders, can be particularly useful.

III. Biologically Active Variants

Biologically active variants of the various compounds disclosed herein as active agents are particularly also encompassed by the invention. Such variants should retain the general biological activity of the original compounds; however, the presence of additional activities would not necessarily limit the use thereof in the present invention. Such activity may be evaluated using standard testing methods and bioassays recognizable by the skilled artisan in the field as generally being useful for identifying such activity.

According to one embodiment of the invention, suitable biologically active variants comprise analogues and derivatives of the compounds described herein. Indeed, a single compound, such as those described herein, may give rise to an entire family of analogues or derivatives having similar activity and, therefore, usefulness according to the present invention. Likewise, a single compound, such as those described herein, may represent a single family member of a greater class of compounds useful according to the present invention. Accordingly, the present invention fully encompasses not only the compounds described herein, but analogues and derivatives of such compounds, particularly those identifiable by methods commonly known in the art and recognizable to the skilled artisan.

The compounds disclosed herein as active agents may contain chiral centers, which may be either of the (R) or (S) configuration, or may comprise a mixture thereof.

Accordingly, the present invention also includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds of the present invention. Isomers may include geometric isomers. Examples of geometric isomers include, but are not limited to, cis isomers or trans isomers across a double bond. Other isomers are contemplated among the compounds of the present invention. The isomers may be used either in pure form or in admixture with other isomers of the compounds described herein.

Various methods are known in the art for preparing optically active forms and determining activity. Such methods include standard tests described herein other similar tests which are will known in the art. Examples of methods that can be used to obtain optical isomers of the compounds according to the present invention include the following:

i) physical separation of crystals whereby macroscopic crystals of the individual enantiomers are manually separated. This technique may particularly be used when crystals of the separate enantiomers exist (i.e., the material is a conglomerate), and the crystals are visually distinct;

ii) simultaneous crystallization whereby the individual enantiomers are separately crystallized from a solution of the racemate, possible only if the latter is a conglomerate in the solid state;

iii) enzymatic resolutions whereby partial or complete separation of a racemate by virtue of differing rates of reaction for the enantiomers with an enzyme;

iv) enzymatic asymmetric synthesis, a synthetic technique whereby at least one step of the synthesis uses an enzymatic reaction to obtain an enantiomerically pure or enriched synthetic precursor of the desired enantiomer;

v) chemical asymmetric synthesis whereby the desired enantiomer is synthesized from an achiral precursor under conditions that produce asymmetry (i.e., chirality) in the product, which may be achieved using chiral catalysts or chiral auxiliaries;

vi) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers;

viii) kinetic resolutions comprising partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors whereby the desired enantiomer is obtained from non-chiral starting materials and where the stereochemical integrity is not or is only minimally compromised over the course of the synthesis;

x) chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography whereby the racemate is volatilized and enantiomers are separated by virtue of their differing interactions in the gaseous mobile phase with a column containing a fixed non-racemic chiral adsorbent phase;

xii) extraction with chiral solvents whereby the enantiomers are separated by virtue of preferential dissolution of one enantiomer into a particular chiral solvent; and xiii) transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The compound optionally may be provided in a composition that is enantiomerically enriched, such as a mixture of enantiomers in which one enantiomer is present in excess, in particular to the extent of 95% or more, or 98% or more, including 100%.

The compounds described herein as active agents can also be in the form of an ester, amide, salt, solvate, prodrug, or metabolite provided they maintain pharmacological activity according to the present invention. Esters, amides, salts, solvates, prodrugs, and other derivatives of the compounds of the present invention may be prepared according to methods generally known in the art, such as, for example, those methods described by J. March, Advanced Organic Chemistry: Reactions, Mechanisms and Structure, $4^{th}$ Ed. (New York: Wiley-Interscience, 1992), which is incorporated herein by reference.

Examples of pharmaceutically acceptable salts of the compounds useful according to the invention include acid addition salts. Salts of non-pharmaceutically acceptable acids, however, may be useful, for example, in the preparation and purification of the compounds. Suitable acid addition salts according to the present invention include organic and inorganic acids. Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzesulfonic, and isethionic acids. Other useful acid addition salts include propionic acid, glycolic acid, oxalic acid, malic acid, malonic acid, benzoic acid, cinnamic acid, mandelic acid, salicylic acid, and the like. Particular example of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

An acid addition salt may be reconverted to the free base by treatment with a suitable base. Preparation of basic salts of acid moieties which may be present on a compound useful according to the present invention may be prepared in a similar manner using a pharmaceutically acceptable base, such as sodium hydroxide, potassium hydroxide, ammonium hydroxide, calcium hydroxide, triethylamine, or the like.

Esters of the active agent compounds according to the present invention may be prepared through functionalization of hydroxyl and/or carboxyl groups that may be present within the molecular structure of the compound. Amides and prodrugs may also be prepared using techniques known to those skilled in the art. For example, amides may be prepared from esters, using suitable amine reactants, or they may be prepared from anhydride or an acid chloride by reaction with ammonia or a lower alkyl amine. Moreover, esters and amides of compounds of the invention can be made by reaction with a carbonylating agent (e.g., ethyl formate, acetic anhydride, methoxyacetyl chloride, benzoyl chloride, methyl isocyanate, ethyl chloroformate, methanesulfonyl chloride) and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0° C. to 60° C. Prodrugs are typically prepared by covalent attachment of a moiety, which results in a compound that is therapeutically inactive until modified by an individual's metabolic system. Examples of pharmaceutically acceptable solvates include, but are not limited to, compounds according to the invention in combination with water, isopropanol, ethanol, methanol, DMSO, ethyl acetate, acetic acid, or ethanolamine.

In the case of solid compositions, it is understood that the compounds used in the methods of the invention may exist in different forms. For example, the compounds may exist in stable and metastable crystalline forms and isotropic and amorphous forms, all of which are intended to be within the scope of the present invention.

If a compound useful as an active agent according to the invention is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such a p-toluenesulfonic acid or ethanesulfonic acid, or the like.

If a compound described herein as an active agent is an acid, the desired salt may be prepared by any suitable method known to the art, including treatment of the free acid with an inorganic or organic base, such as an amine (primary, secondary or tertiary), an alkali metal or alkaline earth metal hydroxide or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum and lithium.

The present invention further includes prodrugs and active metabolites of the active agent compounds described herein. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound. In preferred embodiments, the compounds of this invention possess anti-proliferative activity against abnormally proliferating cells, or are metabolized to a compound that exhibits such activity.

A number of prodrug ligands are known. In general, alkylation, acylation, or other lipophilic modification of one or more heteroatoms of the compound, such as a free amine or carboxylic acid residue, reduces polarity and allows passage into cells. Examples of substituent groups that can replace one or more hydrogen atoms on the free amine and/or carboxylic acid moiety include, but are not limited to, the following: aryl; steroids; carbohydrates (including sugars); 1,2-diacylglycerol; alcohols; acyl (including lower acyl); alkyl (including lower alkyl); sulfonate ester (including alkyl or arylalkyl sulfonyl, such as methanesulfonyl and benzyl, wherein the phenyl group is optionally substituted with one or more substituents as provided in the definition of an aryl given herein); optionally substituted arylsulfonyl; lipids (including phospholipids); phosphotidylcholine; phosphocholine; amino acid residues or derivatives; amino acid acyl residues or derivatives; peptides; cholesterols; or other pharmaceutically acceptable leaving groups which, when administered in vivo, provide the free amine and/or carboxylic acid moiety. Any of these can be used in combination with the disclosed active agents to achieve a desired effect.

IV. Pharmaceutical Compositions

While it is possible for individual active agent compounds used in the methods of the present invention to be administered in the raw chemical form, it is preferred for the compounds to be delivered as a pharmaceutical composition. Accordingly, there are provided by the present invention pharmaceutical compositions comprising one or more compounds described herein as active agents. As such, the compositions used in the methods of the present invention comprise the pharmaceutically active compounds, as described above, or pharmaceutically acceptable esters, amides, salts, solvates, analogs, derivatives, or prodrugs thereof. Further, the compositions can be prepared and delivered in a variety of combinations. For example, the composition can comprise a single composition containing all of the active agents. Alternately, the composition can comprise multiple compositions comprising separate active agents but intended to be administered simultaneously, in succession, or in otherwise close proximity of time.

The active agent compounds described herein can be prepared and delivered together with one or more pharmaceutically acceptable carriers therefore, and optionally, other therapeutic agents. Carriers should be acceptable in that they are compatible with any other agents of the composition and not harmful to the recipient thereof. A carrier may also reduce any undesirable side effects of the agent. Such carriers are known in the art. See, Wang et al. (1980) *J. Parent. Drug Assn.* 34(6):452-462, herein incorporated by reference in its entirety.

Compositions may include short-term, rapid-onset, rapid-offset, controlled release, sustained release, delayed release, and pulsatile release compositions, providing the compositions achieve administration of a compound as described herein. See *Remington's Pharmaceutical Sciences* (18$^{th}$ ed.; Mack Publishing Company, Eaton, Pa., 1990), herein incorporated by reference in its entirety.

Pharmaceutical compositions for use in the methods of the invention are suitable for various modes of delivery, including oral, parenteral (including intravenous, intramuscular, subcutaneous, intradermal, intra-articular, intra-synovial, intrathecal, intra-arterial, intracardiac, subcutaneous, intraorbital, intracapsular, intraspinal, intrasternal, and transdermal), topical (including dermal, buccal, and sublingual), vaginal, urethral, and rectal administration. Administration can also be via nasal spray, surgical implant, internal surgical paint, infusion pump, or via catheter, stent, balloon or other delivery device. The most useful and/or beneficial mode of administration can vary, especially depending upon the condition of the recipient and the disorder being treated.

The pharmaceutical compositions may be conveniently made available in a unit dosage form, whereby such compositions may be prepared by any of the methods generally known in the pharmaceutical arts. Generally speaking, such methods of preparation comprise combining (by various methods) the active compounds of the invention with a suitable carrier or other adjuvant, which may consist of one or more ingredients. The combination of the active agents with the one or more adjuvants is then physically treated to present the composition in a suitable form for delivery (e.g., shaping into a tablet or forming an aqueous suspension).

Pharmaceutical compositions suitable for oral dosage may take various forms, such as tablets, capsules, caplets, and wafers (including rapidly dissolving or effervescing), each containing a predetermined amount of the active agent. The compositions may also be in the form of a powder or granules, a solution or suspension in an aqueous or non-aqueous liquid, and as a liquid emulsion (oil-in-water and water-in-oil). The active agents may also be delivered as a bolus, electuary, or paste. It is generally understood that methods of preparations of the above dosage forms are generally known in the art, and any such method would be suitable for the preparation of the respective dosage forms for use in delivery of the compositions according to the present invention.

In one embodiment, an active agent compound may be administered orally in combination with a pharmaceutically acceptable vehicle such as an inert diluent or an edible carrier. Oral compositions may be enclosed in hard or soft shell gelatin capsules, may be compressed into tablets or may be incorporated directly with the food of the patient's diet. The percentage of the composition and preparations may be varied; however, the amount of substance in such therapeutically useful compositions is preferably such that an effective dosage level will be obtained.

Hard capsules containing the active agent compounds may be made using a physiologically degradable composition, such as gelatin. Such hard capsules comprise the compound, and may further comprise additional ingredients including, for example, an inert solid diluent such as calcium carbonate, calcium phosphate, or kaolin. Soft gelatin capsules containing the compound may be made using a physiologically degradable composition, such as gelatin. Such soft capsules comprise the compound, which may be mixed with water or an oil medium such as peanut oil, liquid paraffin, or olive oil.

Sublingual tablets are designed to dissolve very rapidly. Examples of such compositions include ergotamine tartrate, isosorbide dinitrate, and isoproterenol HCL. The compositions of these tablets contain, in addition to the drug, various soluble excipients, such as lactose, powdered sucrose, dextrose, and mannitol. The solid dosage forms of the present invention may optionally be coated, and examples of suitable coating materials include, but are not limited to, cellulose polymers (such as cellulose acetate phthalate, hydroxypropyl cellulose, hydroxypropyl methylcellulose, hydroxypropyl methylcellulose phthalate, and hydroxypropyl methylcellulose acetate succinate), polyvinyl acetate phthalate, acrylic acid polymers and copolymers, and methacrylic resins (such as those commercially available under the trade name EUDRAGIT®), zein, shellac, and polysaccharides.

Powdered and granular compositions of a pharmaceutical preparation may be prepared using known methods. Such compositions may be administered directly to a patient or used in the preparation of further dosage forms, such as to form tablets, fill capsules, or prepare an aqueous or oily suspension or solution by addition of an aqueous or oily vehicle thereto. Each of these compositions may further comprise one or more additives, such as dispersing or wetting agents, suspending agents, and preservatives. Additional excipients (e.g., fillers, sweeteners, flavoring, or coloring agents) may also be included in these compositions.

Liquid compositions of pharmaceutical compositions which are suitable for oral administration may be prepared, packaged, and sold either in liquid form or in the form of a dry product intended for reconstitution with water or another suitable vehicle prior to use.

A tablet containing one or more active agent compounds described herein may be manufactured by any standard process readily known to one of skill in the art, such as, for example, by compression or molding, optionally with one or more adjuvant or accessory ingredient. The tablets may optionally be coated or scored and may be formulated so as to provide slow or controlled release of the active agents.

Adjuvants or accessory ingredients for use in the compositions can include any pharmaceutical ingredient commonly deemed acceptable in the art, such as binders, fillers, lubricants, disintegrants, diluents, surfactants, stabilizers, preservatives, flavoring and coloring agents, and the like. Binders are generally used to facilitate cohesiveness of the tablet and ensure the tablet remains intact after compression. Suitable binders include, but are not limited to: starch, polysaccharides, gelatin, polyethylene glycol, propylene glycol, waxes, and natural and synthetic gums. Acceptable fillers include silicon dioxide, titanium dioxide, alumina, talc, kaolin, powdered cellulose, and microcrystalline cellulose, as well as soluble materials, such as mannitol, urea, sucrose, lactose, dextrose, sodium chloride, and sorbitol. Lubricants are useful for facilitating tablet manufacture and include vegetable oils, glycerin, magnesium stearate, calcium stearate, and stearic acid. Disintegrants, which are useful for facilitating disintegration of the tablet, generally include starches, clays, celluloses, algins, gums, and crosslinked polymers. Diluents, which are generally included to provide bulk to the tablet, may include dicalcium phosphate, calcium sulfate, lactose, cellulose, kaolin, mannitol, sodium chloride, dry starch, and powdered sugar. Surfactants suitable for use in the composition according to the present invention may be anionic, cationic, amphoteric, or nonionic surface active agents. Stabilizers may be included in the compositions to inhibit or lessen reactions leading to decomposition of the active agents, such as oxidative reactions.

Solid dosage forms may be formulated so as to provide a delayed release of the active agents, such as by application of a coating. Delayed release coatings are known in the art, and dosage forms containing such may be prepared by any known suitable method. Such methods generally include that, after preparation of the solid dosage form (e.g., a tablet or caplet), a delayed release coating composition is applied. Application can be by methods, such as airless spraying, fluidized bed coating, use of a coating pan, or the like. Materials for use as a delayed release coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof.

Solid dosage forms according to the present invention may also be sustained release (i.e., releasing the active agents over a prolonged period of time), and may or may not also be delayed release. Sustained release compositions are known in the art and are generally prepared by dispersing a drug within a matrix of a gradually degradable or hydrolyzable material, such as an insoluble plastic, a hydrophilic polymer, or a fatty compound. Alternatively, a solid dosage form may be coated with such a material.

Compositions for parenteral administration include aqueous and non-aqueous sterile injection solutions, which may further contain additional agents, such as anti-oxidants, buffers, bacteriostats, and solutes, which render the compositions isotonic with the blood of the intended recipient. The compositions may include aqueous and non-aqueous sterile suspensions, which contain suspending agents and thickening agents. Such compositions for parenteral administration may be presented in unit-dose or multi-dose containers, such as, for example, sealed ampoules and vials, and may be stores in a freeze-dried (lyophilized) condition requiring only the addition of the sterile liquid carrier, for example, water (for injection), immediately prior to use. Extemporaneous injection solutions and suspensions may be prepared from sterile powders, granules, and tablets of the kind previously described.

The compositions for use in the methods of the present invention may also be administered transdermally, wherein the active agents are incorporated into a laminated structure (generally referred to as a "patch") that is adapted to remain in intimate contact with the epidermis of the recipient for a prolonged period of time. Typically, such patches are available as single layer "drug-in-adhesive" patches or as multilayer patches where the active agents are contained in a layer separate from the adhesive layer. Both types of patches also generally contain a backing layer and a liner that is removed prior to attachment to the skin of the recipient. Transdermal drug delivery patches may also be comprised of a reservoir underlying the backing layer that is separated from the skin of the recipient by a semi-permeable membrane and adhesive layer. Transdermal drug delivery may occur through passive diffusion or may be facilitated using electrotransport or iontophoresis.

Compositions for rectal delivery include rectal suppositories, creams, ointments, and liquids. Suppositories may be presented as the active agents in combination with a carrier generally known in the art, such as polyethylene glycol. Such dosage forms may be designed to disintegrate rapidly or over an extended period of time, and the time to complete disintegration can range from a short time, such as about 10 minutes, to an extended period of time, such as about 6 hours.

Topical compositions may be in any form suitable and readily known in the art for delivery of active agents to the body surface, including dermally, buccally, and sublingually. Typical examples of topical compositions include ointments, creams, gels, pastes, and solutions. Compositions for topical administration in the mouth also include lozenges.

In certain embodiments, the compounds and compositions disclosed herein can be delivered via a medical device. Such delivery can generally be via any insertable or implantable medical device, including, but not limited to stents, catheters, balloon catheters, shunts, or coils. In one embodiment, the present invention provides medical devices, such as stents, the surface of which is coated with a compound or composition as described herein. The medical device of this invention can be used, for example, in any application for treating, preventing, or otherwise affecting the course of a disease or condition, such as those disclosed herein.

In another embodiment of the invention, pharmaceutical compositions comprising one or more active agents described herein are administered intermittently. Administration of the therapeutically effective dose may be achieved in a continuous manner, as for example with a sustained-release composition, or it may be achieved according to a desired daily dosage regimen, as for example with one, two, three, or more administrations per day. By "time period of discontinuance" is intended a discontinuing of the continuous sustained-released or daily administration of the composition. The time period of discontinuance may be longer or shorter than the period of continuous sustained-release or daily administration. During the time period of discontinuance, the level of the components of the composition in the relevant tissue is substantially below the maximum level obtained during the treatment. The preferred length of the discontinuance period depends on the concentration of the effective dose and the form of composition used. The discontinuance period can be at least 2 days, at least 4 days or at least 1 week. In other embodiments, the period of discontinuance is at least 1 month, 2 months, 3 months, 4 months or greater. When a sustained-release composition is used, the discontinuance period must be extended to account for the greater residence time of the composition in the body. Alternatively, the frequency of administration of the effective dose of the sustained-release composition can be decreased accordingly. An intermittent schedule of administration of a composition of the invention can continue until the desired therapeutic effect, and ultimately treatment of the disease or disorder, is achieved.

Administration of the composition comprises administering a pharmaceutically active agent as described herein or administering one or more pharmaceutically active agents described herein in combination with one or more further pharmaceutically active agents (i.e., co-administration). Accordingly, it is recognized that the pharmaceutically active agents described herein can be administered in a fixed combination (i.e., a single pharmaceutical composition that contains both active agents). Alternatively, the pharmaceutically active agents may be administered simultaneously (i.e., separate compositions administered at the same time). In another embodiment, the pharmaceutically active agents are administered sequentially (i.e., administration of one or more pharmaceutically active agents followed by separate administration or one or more pharmaceutically active agents). One of skill in the art will recognized that the most preferred method of administration will allow the desired therapeutic effect.

Delivery of a therapeutically effective amount of a composition according to the invention may be obtained via administration of a therapeutically effective dose of the composition. Accordingly, in one embodiment, a therapeutically effective amount is an amount effective to treat fibromyalgia. In another embodiment, a therapeutically effective amount is an amount effective to treat a symptom of fibromyalgia. In yet another embodiment, a therapeutically effective amount is an amount effective to treat chronic pain generally. In further embodiments, a therapeutically effective amount is an amount effective to treat muscle pain, joint pain, or neurologic pain. In still another embodiment, a therapeutically effective amount is an amount effective to treat fatigue.

The active agents included in the pharmaceutical composition are present in an amount sufficient to deliver to a patient a therapeutic amount of an active agent in vivo in the absence of serious toxic effects. The concentration of active agent in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active agent may be administered at once, or may be divided into a number of smaller doses to be administered at varying intervals of time A therapeutically effective amount according to the invention can be determined based on the bodyweight of the recipient. Alternatively, a therapeutically effective amount can be described in terms of a fixed dose. In still further embodiments, a therapeutically effective amount of one or more active agents disclosed herein can be described in terms of the peak plasma concentration achieved by administration of the active agents. Of course, it is understood that the therapeutic amount could be divided into a number of fractional dosages administered throughout the day. The effective dosage range of pharmaceutically acceptable salts and prodrugs can be calculated based on the weight of the parent nucleoside to be delivered. If a salt or prodrug exhibits activity in itself, the effective dosage can be estimated as above using the weight of the salt or prodrug, or by other means known to those skilled in the art.

It is contemplated that compositions of the invention comprising one or more active agents described herein will be administered in therapeutically effective amounts to a mammal, preferably a human. An effective dose of a compound or composition for treatment of any of the conditions or diseases described herein can be readily determined by the use of conventional techniques and by observing results obtained under analogous circumstances. The effective amount of the compositions would be expected to vary according to the weight, sex, age, and medical history of the subject. Of course, other factors could also influence the effective amount of the composition to be delivered, including, but not limited to, the specific disease involved, the degree of involvement or the severity of the disease, the response of the individual patient, the particular compound administered, the mode of administration, the bioavailability characteristics of the preparation administered, the dose regimen selected, and the use of concomitant medication. The compound is preferentially administered for a sufficient time period to alleviate the undesired symptoms and the clinical signs associated with the condition being treated. Methods to determine efficacy and dosage are known to those skilled in the art. See, for example, Isselbacher et al. (1996) *Harrison's Principles of Internal Medicine* 13 ed., 1814-1882, herein incorporated by reference.

In certain embodiments, a therapeutically effective amount of droxidopa comprises about 10 mg to about 3 g. Such therapeutically effective amount represents an amount of droxidopa that would be provided in a single dose when used as part of a combination according to the invention. It is understood that when the droxidopa is provided as a salt, ester, amide, or other pharmaceutically acceptable form, the amount of the pharmaceutical form of droxidopa can vary to the extent necessary to deliver a therapeutically effective amount of droxidopa. Further, as the therapeutically effective amount of droxidopa is provided as an amount for a single dose, the dosage amounts indicated herein do not necessarily represent the maximum amount of droxidopa that may be administered over the course of a 24 hour period since it is possible that multiple doses of the combination may be indicated for treatment of various conditions.

In further embodiments, the therapeutically effective amount of droxidopa can encompass varying ranges, and the appropriate range could be determined based upon the severity of the condition being treated and the one or more additional compounds with which the droxidopa is combined. In specific embodiments, a therapeutically effective amount of droxidopa comprises about 10 mg to about 2 g, about 10 mg to about 1 g, about 20 mg to about 900 mg, about 30 mg to about 850 mg, about 40 mg to about 800 mg, about 50 mg to about 750 mg, about 60 mg to about 700 mg, about 70 mg to about 650 mg, about 80 mg to about 600 mg, about 90 mg to about 550 mg, about 100 mg to about 500 mg, about 100 mg to about 400 mg, or about 100 mg to about 300 mg.

In yet other embodiments, a therapeutically effective amount of droxidopa can be even greater, such as when provided as a sustained-, extended-, or continuous-release formulation. As understood in the art, such formulations provide an increased drug amount in a single dosage form that slowly releases the drug over time. A therapeutically effective amount of droxidopa for use in such a formulation can be calculated in light of the effective amounts described above and the determined frequency of dosing that would otherwise be necessary to treat a given condition.

A therapeutically effective amount of the one or more additional compounds that are combined with droxidopa according to the invention can be determined in relation to the amount of droxidopa included in the dosage form and the desired ratio of droxidopa to the additional compound(s). Advantageously, the present invention allows for great flexibility in formulating combinations. For example, the conserving effects provided by the one or more additional compounds can allow for using droxidopa in a lesser amount and still achieve the same, or better, therapeutic effects achieved using droxidopa alone. Likewise, it is possible to increase the therapeutic effects of droxidopa by using an amount of the one or more additional compounds that is less than the typically recommended dosage for the one or more additional compounds.

In one embodiment, the ratio of droxidopa to the one or more additional compounds is in the range of about 500:1 to about 1:10. In further embodiments, the ratio of droxidopa to the additional compound(s) is in the range of about 250:1 to about 1:5, about 100:1 to about 1:2, about 80:1 to about 1:1, about 50:1 to about 2:1, or about 20:1 to about 3:1.

The one or more additional compounds combined with droxidopa according to the invention can be included in amount typically recommended for use of the compounds alone for other indications. However, as noted above, it is possible according to the invention to use the additional compound(s) in amounts that are less than typically recommended, particularly in relation to DDC inhibitors, COMT inhibitors, cholinesterase inhibitors, and MAO inhibitors. In certain embodiments, a therapeutically effective amount of a DDC inhibitor, COMT inhibitor, cholinesterase inhibitor, or MAO inhibitor to be combined with droxidopa is in the range of about 1 mg to about 200 mg. Of course, this range is exemplary and could vary depending upon the amount of droxidopa included in the combination and the desired ratio of the compounds in the combination, as described above.

As noted above, droxidopa may also be combined with other active agents that can provide complimentary effects for the treatment of fibromyalgia (e.g., antidepressants, anti-inflammatories, muscle relaxants, antibiotics, mood stabilizers, antipsychotics, 5-HT2 and 5-HT3 antagonists, 5-HT1A receptor agonists, pain relievers, caffeine; NMDA receptor ligands, s-adenosyl-methionine; zopiclone; chlormezanone; proglumetacin; 5-OH-L-tryptophan; gabapentin, pregabalin, and tamoxefin). When such complimentary active agents are used, they can be included in amounts typically prescribed for their respective uses.

V. Articles of Manufacture

The present invention also includes an article of manufacture providing a composition comprising one or more active agents described herein. The article of manufacture can include a vial or other container that contains a composition suitable for use according to the present invention together with any carrier, either dried or in liquid form. In particular, the article of manufacture can comprise a kit including a container with a composition according to the invention. In such a kit, the composition can be delivered in a variety of combinations. For example, the composition can comprise a single dosage comprising all of the active agents. Alternately, where more than one active agent is provided, the composition can comprise multiple dosages, each comprising one or more active agents, the dosages being intended for administration in combination, in succession, or in other close proximity of time. For example, the dosages could be solid forms (e.g., tablets, caplets, capsules, or the like) or liquid forms (e.g., vials), each comprising a single active agent, but being provided in blister packs, bags, or the like, for administration in combination.

The article of manufacture further includes instructions in the form of a label on the container and/or in the form of an insert included in a box in which the container is packaged, for the carrying out the method of the invention. The instructions can also be printed on the box in which the vial is packaged. The instructions contain information such as sufficient dosage and administration information so as to allow the subject or a worker in the field to administer the pharmaceutical composition. It is anticipated that a worker in the field encompasses any doctor, nurse, technician, spouse, or other caregiver that might administer the composition. The pharmaceutical composition can also be self-administered by the subject.

EXPERIMENTAL

The present invention will now be described with specific reference to various examples. The following examples are not intended to be limiting of the invention and are rather provided as exemplary embodiments.

Example 1

Effective Treatment of Chronic Pain Through Administration of Droxidopa in Combination with Carbidopa Treatment of fibromyalgia through reducing sensitivity to chronic pain using droxidopa in combination with carbidopa was investigated using the Chronic Constriction Injury (CCI) model. Male Wistar rats weighing 160 to 200 grams were used, and CCI was induced using the methods described in Bennett and Xie (*Pain*, 33(1): 87-107). Specifically, after anesthetization using pentobarbital (50 mg/kg, 5 ml/kg, i.p.), the sciatic nerve was exposed at mid-thigh level, and three ligatures (4-0 silk suture), about 1 mm apart, were loosely tied around the nerve. The animals were then housed individually in cages with soft bedding for seven days before testing for mechanical allodynia.

On the test day, rats were placed under inverted Plexiglas cages on a wire mesh rack and allowed to acclimate for 20 to 30 minutes. Mechanical allodynia was evaluated by responsiveness to a #12 Supertip (IITC, USA) applied through the mesh floor perpendicular to the central plantar surface of the left hind paw. The tip was gradually applied with sufficient force to cause slight buckling of the filament against the paw. A positive response to the applied tactile pressure, noted by sharp withdrawal of the paw, was recorded automatically by an Electronic Von Frey Anesthesiometer (2290CE ELECTROVONFREY®, IITC, USA).

Rats were pre-selected (clear presence of allodynia) for experimentation only if the nociceptive response seven days after nerve ligation (pre-treatment) was reduced by 10 grams of force relative to the response of the individual paw before nerve ligation (pre-ligation. Treatment was with 1) 5 ml/kg of a pharmaceutical vehicle (2% TWEEN® 80 and 0.9% NaCl), 2) 400 mg/kg of droxidopa and 20 mg/kg of carbidopa, or 3) 18 mg/kg of fluoxetine. The treatments were administered by IP injection to groups of 10 animals and the level of allodynia was determined at 60 minutes post dosing.

Allodynia was calculated according to the following formula:

$$\% \text{ Inhibition} = \Delta\text{Treatment}/\Delta\text{Blank} \times 100\%.$$

where $\Delta$ Treatment is the change in tactile pressure threshold over pre-treatment after ligation [(Post-Treatment)−(Pre-Treatment)], and $\Delta$ Blank is change in tactile pressure threshold over pre-ligation but before treatment [(Pre-Ligation)−(Pre-Treatment)]. A one-way ANOVA followed by t-test was applied for comparison between test substance treated groups and the vehicle control group. Activity was considered significant at $P<0.05$.

Rats from all groups developed marked allodynia following the CCI procedure with an average change in tactile response of greater than 20 for each group (range=12.7-26.3), as illustrated in Table 1. Animals in the vehicle treatment group had no change in the level of allodynia observed pre- and post-treatment ($p>0.7$). The percent inhibition of allodynia was significantly different between the three groups by ANOVA ($p<0.0001$). Animals treated with fluoxetine were not significantly different from vehicle-treated rats. In contrast, animals treated with 400 mg/kg of Droxidopa plus 20 mg/kg Carbidopa had significantly decreased levels of allodynia when compared with vehicle treated animals ($p<0.0001$). The percent inhibition of allodynia in the three groups is illustrated in FIG. 1.

TABLE 1

| Treatment | N | B.W. | (1) Pre-Ligation | (2) Pre-Treatment | (1) − (2) | (3) Post-Treatment | (3) − (2) | Inhibition (%) |
|---|---|---|---|---|---|---|---|---|
| Vehicle - | 1 | 199 | 24.7 | 7.8 | 16.9 | 8.6 | 0.8 | 4.7 |
| 2% TWEEN ® 80, | 2 | 191 | 25.1 | 12.4 | 12.7 | 9.1 | −3.3 | −26.0 |
| 0.9% NaCl | 3 | 187 | 27.4 | 5.6 | 21.8 | 6.6 | 1 | 4.6 |
| | 4 | 203 | 34.4 | 12.1 | 22.3 | 8.5 | −3.6 | −16.1 |
| | 5 | 205 | 31.6 | 6.3 | 25.3 | 10.5 | 4.2 | 16.6 |
| | 6 | 215 | 24.4 | 11 | 13.4 | 5.2 | −5.8 | −43.3 |
| | 7 | 201 | 29.4 | 10.5 | 18.9 | 7.6 | −2.9 | −15.3 |
| | 8 | 208 | 30.6 | 7 | 23.6 | 7.4 | 0.4 | 1.7 |
| | 9 | 184 | 29.4 | 9.7 | 19.7 | 10.1 | 0.4 | 2.0 |

TABLE 1-continued

| Treatment | N | B.W. | (1) Pre-Ligation | (2) Pre-Treatment | (1) − (2) | (3) Post-Treatment | (3) − (2) | Inhibition (%) |
|---|---|---|---|---|---|---|---|---|
|  | 10 | 205 | 32.9 | 7.7 | 25.2 | 13 | 5.3 | 21.0 |
|  |  | Ave. | 29.0 | 9.0 | 20.0 | 8.7 | −0.4 | −5.0 |
|  |  | SEM | 1.1 | 0.8 | 1.4 | 0.7 | 1.1 | 6.3 |
| Droxidopa | 1 | 218 | 25.6 | 10.1 | 15.5 | 26.3 | 16.2 | 104.5 |
|  | 2 | 178 | 28.8 | 7.7 | 21.1 | 32.1 | 24.4 | 115.6 |
|  | 3 | 190 | 31.9 | 6.7 | 25.2 | 23.4 | 16.7 | 66.3 |
|  | 4 | 184 | 30.8 | 11.8 | 19 | 26.2 | 14.4 | 75.8 |
|  | 5 | 178 | 28.5 | 6.6 | 21.9 | 22.9 | 16.3 | 74.4 |
|  | 6 | 211 | 32.9 | 8.6 | 24.3 | 11.4 | 2.8 | 11.5 |
|  | 7 | 212 | 25.3 | 6.3 | 19 | 20.1 | 13.8 | 72.6 |
|  | 8 | 180 | 29.6 | 6.6 | 23 | 12.6 | 6 | 26.1 |
|  | 9 | 196 | 28.9 | 11.4 | 17.5 | 22.3 | 10.9 | 62.3 |
|  | 10 | 197 | 31.5 | 8.8 | 22.7 | 19.7 | 10.9 | 48.0 |
|  |  | Ave. | 29.4 | 8.5 | 20.9 | 21.7 | 13.2 | 65.7 |
|  |  | SEM | 0.8 | 0.6 | 1.0 | 2.0 | 1.9 | 10.0 |
| Fluoxetine | 1 | 177 | 30.3 | 9.1 | 21.2 | 14.4 | 5.3 | 25.0 |
|  | 2 | 204 | 31.5 | 11.2 | 20.3 | 12.4 | 1.2 | 5.9 |
|  | 3 | 186 | 25.5 | 8.2 | 17.3 | 11.2 | 3 | 17.3 |
|  | 4 | 201 | 24.7 | 9.1 | 15.6 | 9.7 | 0.6 | 3.8 |
|  | 5 | 210 | 31.7 | 5.4 | 26.3 | 7 | 1.6 | 6.1 |
|  | 6 | 198 | 32.0 | 7.4 | 24.6 | 10.4 | 3 | 12.2 |
|  | 7 | 176 | 25.7 | 12 | 13.7 | 6.5 | −5.5 | −40.1 |
|  | 8 | 190 | 24.2 | 8.2 | 16 | 8.8 | 0.6 | 3.8 |
|  | 9 | 225 | 31.1 | 8.7 | 22.4 | 6 | −2.7 | −12.1 |
|  | 10 | 191 | 34.1 | 9.5 | 24.6 | 5.9 | −3.6 | −14.6 |
|  |  | Ave. | 29.1 | 8.9 | 20.2 | 9.2 | 0.4 | 0.7 |
|  |  | SEM | 1.2 | 0.6 | 1.4 | 0.9 | 1.1 | 5.9 |

As seen in Table 1 and illustrated in FIG. 1, treatment according to the invention resulted in total allodynia inhibition in several test subjects. The average percentage inhibition using the inventive method was almost 66%. By contrast, treatment using the control vehicle resulted in an average increase in allodynia of 5%. Two test subjects treated with the vehicle showed 16.6% and 21% inhibition, but other test subjects treated with the vehicle exhibited increases in allodynia of 15.3%, 16.1%, 26.0%, and even 43.3%. Similarly, treatment with fluoxetine resulted in an average allodynia inhibition of less than 1%. Again, one test subject treated with fluoxetine exhibited allodynia inhibition of 25%; however, other fluoxetine-treated subjects exhibited increases in allodynia of as much as 40.1%.

Example 2

Pharmacokinetic Properties of Droxidopa Combinations

The pharmacokinetic properties of droxidopa combinations useful in the methods of the invention were evaluated in male Sprague Dawley rats. Four test groups with four rats in each group were established. Group 1 was administered droxidopa alone as a baseline group. Group 2 was administered droxidopa in combination with the COMT inhibitor entacapone. Group 3 was administered droxidopa in combination with the cholinesterase inhibitor pyridostigmine. Group 4 was administered droxidopa in combination with the MAOI nialamide. For each group, the droxidopa or droxidopa combination was formulated with a vehicle formed of a water solution containing 1% carboxymethylcellulose with 0.2% TWEEN® 80 emulsifier.

The weights and of the droxidopa, entacapone, pyridostigmine, nialamide, and the vehicle provided in the various formulations are shown in Table 2. The calculated concentrations for each component are separately provided in Table 3. The amounts of entacapone, pyridostigmine, and nialamide used in formulations 2-7 were provided as "low" doses and "high" doses based upon disclosure in the literature of generally accepted dosage ranges for their respective known indications.

TABLE 2

| Formulation | Formulation Components - weight (g) | | | | |
|---|---|---|---|---|---|
|  | Vehicle | Droxidopa | Entacapone | Pyridostigmine | Nialamide |
| 1 | 13.87 g | 0.280 g |  |  |  |
| 2 | 13.65 g | 0.280 g | 0.0084 g |  |  |
| 3 | 13.60 g | 0.280 g | 0.0842 g |  |  |
| 4 | 13.53 g | 0.280 g |  | 0.0028 g |  |
| 5 | 13.60 g | 0.280 g |  | 0.0563 g |  |
| 6 | 13.61 g | 0.280 g |  |  | 0.0028 g |
| 7 | 13.70 g | 0.280 g |  |  | 0.0842 g |

TABLE 3

| Formulation | Formulation Components - concentration (mg/g) | | | |
|---|---|---|---|---|
|  | Droxidopa | Entacapone | Pyridostigmine | Nialamide |
| 1 | 19.81 mg/g |  |  |  |
| 2 | 20.11 mg/g | 0.603 mg/g |  |  |
| 3 | 20.08 mg/g | 6.031 mg/g |  |  |
| 4 | 20.30 mg/g |  | 0.203 mg/g |  |
| 5 | 20.20 mg/g |  | 4.042 mg/g |  |
| 6 | 20.15 mg/g |  |  | 0.202 mg/g |
| 7 | 20.04 mg/g |  |  | 5.985 mg/g |

Rats in each group were given a single gavage dose of droxidopa alone or the droxidopa combination, the time of dosing being recorded as time=0. Dosing was based upon the weight of the subject and was adjusted to provide all test subjects a droxidopa dose of approximately 100 mg per kg of body weight. Blood samples (approximately 100 μL) were collected at approximately 5, 15, and 30 minutes, and at approximately 1, 2, 4, 8, and 24 hours after dosing. Dosing and blood collection were via an indwelling jugular vein cannula. Blood samples were drawn into a heparinized 1 mL syringe (charged with 5 µL of heparin solution [1000 U/mL]) and then transferred to a microcentrifuge.

Acetonitrile (100 µL) containing 0.2% formic acid was added to 25 µL of each plasma sample in a microcentrifuge tube. Internal standard (5 µL of 4 µg/mL 3,4-dihydroxybenzylamine (DHBA) in acetonitrile) was added, and the samples were vortexed and centrifuged to precipitate protein. The supernatant was transferred to an autosample vial with insert and injected on an Applied Biosystems API 4000 Liquid Chromatography-Mass Spectrometer (LC-MS) apparatus interfaced with an Agilent 100 High Pressure Liquid Chromatography (HPLC) apparatus. Data was collected and processed using Analyst software. The autosampler was cooled to 4° C., and the sample injection volume 5 µL. Chromatography was conducted on a Waters Atlantis dC18 column (25 cm×4.6 mm, 5 µm) with guard column. The solvent was water containing 0.2% formic acid, and the flow rate was set at 0.8 mL/min.

Plasma droxidopa concentration in the rat test subjects following administration of droxidopa alone or droxidopa combinations according to the invention is provided in Table 4. As a standard, plasma droxidopa concentration in rats administered the drug vehicle with no droxidopa or droxidopa combinations present was also evaluated, and no droxidopa was detected over a 24 hour period in plasma from the rats administered the vehicle alone. Likewise, no droxidopa was detected in any subjects prior to dosing of the droxidopa or droxidopa combinations. As seen in Table 4, plasma droxidopa concentration reached a maximum concentration for all formulations in a time of approximately 1-2 hours following dosing.

TABLE 4

Mean Plasma Droxidopa Concentration (µg/mL) at Time Post-Dosage

| Formulation | 0.083 hr | 0.25 hr | 0.5 hr | 1 hr | 2 hr | 4 hr | 8 hr | 24 hr |
|---|---|---|---|---|---|---|---|---|
| 1 | 0.401 | 3.996 | 7.869 | 11.336 | 10.548 | 3.391 | 0.610 | 0.001 |
| 2 | 0.328 | 3.245 | 8.641 | 12.050 | 8.772 | 4.795 | 3.054 | 0.005 |
| 3 | 0.189 | 2.799 | 6.775 | 8.440 | 9.270 | 3.425 | 1.853 | 0.010 |
| 4 | 0.459 | 3.570 | 7.941 | 10.054 | 8.650 | 2.976 | 1.795 | 0.005 |
| 5 | 0.456 | 4.033 | 7.341 | 8.380 | 5.989 | 2.429 | 0.431 | 0.002 |
| 6 | 0.493 | 2.867 | 6.807 | 8.579 | 6.065 | 1.829 | 0.297 | 0.000 |
| 7 | 0.311 | 3.017 | 6.506 | 7.886 | 6.381 | 2.380 | 1.535 | 0.113 |

Administration of droxidopa combinations was seen to affect plasma norepinephrine concentration in comparison to administration of droxidopa alone. Mean plasma norepinephrine concentration at 2 hours post-dosing with the various formulations tested is provided in Table 5. Formulation 0 indicates administration of the vehicle alone without droxidopa or a droxidopa combination of the invention and provides a baseline comparative of plasma norepinephrine levels in an untreated subject.

TABLE 5

| Formulation | Plasma Norepinephrine Concentration (pg/µL) |
|---|---|
| 0 | 0.711 |
| 1 | 3.320 |
| 2 | 3.358 |
| 3 | 6.359 |
| 4 | 4.000 |
| 5 | 2.290 |

TABLE 5-continued

| Formulation | Plasma Norepinephrine Concentration (pg/µL) |
|---|---|
| 6 | 2.182 |
| 7 | 2.674 |

As seen in Table 5, administration of droxidopa alone caused an approximate 5-fold increase in plasma norepinephrine concentration. Treatment with droxidopa in combination with the COMT inhibiting compound caused an even greater increase in plasma norepinephrine concentration. Treatment with droxidopa in combination with a relatively low dose of the cholinesterase inhibiting compound similarly caused an increase in plasma norepinephrine concentration in relation to treatment with droxidopa alone; however, the plasma norepinephrine concentration was reduced in relation to treatment with droxidopa alone when a combination of droxidopa with a relatively high dose of the cholinesterase inhibiting compound was used. Plasma norepinephrine concentration after treatment with both combinations of droxidopa with the MAOI compound was reduced relative to treatment with droxidopa alone.

Mean values for various pharmacokinetic properties of the inventive combinations used in the above study are provided in Table 6. Specifically, Table 6 provides the terminal elimination half-life ($T_{1/2}$) of the administered formulations, the maximum observed concentration ($C_{max}$) of the active agents in each formulation, the time to reach the maximum observed concentration ($T_{max}$), the area under the plasma concentration-time curve from time zero to the last measured time point ($AUC_{all}$), and the observed volume of distribution at steady state (Vz_F_obs). Note that for extravascular models, the fraction of dose absorbed cannot be estimated. Therefore, Vz_F_obs for such models is actually Volume/F where F is the fraction of dose absorbed.

TABLE 6

| Formulation | $T_{1/2}$ (hr) | $C_{max}$ (µg/mL) | $T_{max}$ (hr) | $AUC_{all}$ (hr·µg/mL) | Vz_F_obs (mL/kg) |
|---|---|---|---|---|---|
| 1 | 1.4 | 11.4 | 1.25 | 44.4 | 5270.4 |
| 2 | 1.86 | 12.4 | 1.125 | 71.1 | 5016.4 |
| 3 | 2.64 | 10.2 | 1.38 | 52.3 | 8854.1 |
| 4 | 1.93 | 10.1 | 1.25 | 51.2 | 5900.8 |
| 5 | 1.79 | 8.4 | 1 | 30.5 | 8763.6 |
| 6 | 1.41 | 8.6 | 1 | 27.2 | 8030.0 |
| 7 | 3.77 | 8.1 | 0.875 | 42.0 | 16404.1 |

As seen above, when droxidopa is combined with certain additional active agents, the combination can increase the half-life of droxidopa, and such increase can be seen in a variety of pathways, such as through an effect on drug metabolism, volume of distribution of the drug, or a combination of the two. For example, the increase in half-life arising from the combination with entacapone indicates peripheral activity to block the metabolism of droxidopa to 3-OM-droxidopa (the major metabolite of droxidopa), thus increasing residence time of droxidopa in the body. Similarly, an increase in the volume of distribution indicates a decrease in the amount of drug available to organs of elimination, which can further affect half-life. The increase in half-life associated with the relatively high dose of nialamide is surprising since MAOIs are not typically considered to be a major metabolic pathway for droxidopa, and is likely the result of the unexpected increase in the apparent volume of distribution. Similarly, the combination with pyridostigmine also surprisingly led to an increase in droxidopa half-life even though cholinesterase compounds would generally not be expected to affect droxidopa metabolism. Droxidopa half-life when administered alone or in combination with entacapone, pyridostigmine, or nialamide is graphically illustrated in FIG. 2.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for reducing pain associated with fibromyalgia, the method comprising administering a therapeutically effective amount of droxidopa to a patient suffering from fibromyalgia.

2. The method of claim 1, wherein the fibromyalgia-associated pain is reduced by at least 50%.

3. The method of claim 1, wherein the fibromyalgia-associated pain is reduced by at least 60%.

4. The method of claim 1, further comprising administering one or more additional active agents selected from the group consisting of DOPA decarboxylase inhibiting compounds, catechol-O-methyltransferase inhibitors, cholinesterase inhibitors, antidepressants, anti-inflammatories, muscle relaxants, antibiotics, mood stabilizers, antipsychotics, serotonin receptor antagonists, serotonin receptor agonists, pain relievers, stimulants, NMDA receptor ligands, s-adenosyl-methionine, zopiclone, chlormezanone, proglumetacin, 5-OH-L-tryptophan, gabapentin, pregabalin, tamoxefin, and combinations thereof.

5. The method of claim 4, wherein the one or more additional active agents comprise one or more DOPA decarboxylase inhibiting compounds selected from the group consisting of benserazide, carbidopa, difluoromethyldopa, α-methyldopa, and combinations thereof.

6. The method of claim 4, wherein the one or more additional active agents comprise one or more catechol-O-methyltransferase inhibitors selected from the group consisting of entacapone, tolcapone, nitecapone, and combinations thereof.

7. The method of claim 4, wherein the one or more additional active agents comprise one or more cholinesterase inhibitors selected from the group consisting of pyridostigmine, donepezil, rivastigmine, galantamine, tacrine, neostigmine, metrifonate, physostigmine, ambenonium, edrophonium, demarcarium, thiaphysovenine, phenserine, cymserine, and combinations thereof.

8. The method of claim 4, wherein the one or more additional active agents comprise one or more antidepressants, wherein the antidepressant is a monoamine oxidase inhibitor selected from the group consisting of isocarboxazid, moclobemide, phenelzine, tranylcypromine, selegiline, lazabemide, nialamide, iproniazid, iproclozide, toloxatone, harmala, brofaromine, benmoxin, 5-Methoxy-N,N-dimethyltryptamine, 5-methoxy-α-methyltryptamine, and combinations thereof.

9. The method of claim 4, wherein the one or more additional active agents comprise one or more antidepressants selected from the group consisting of selective serotonin reuptake inhibitors, tricyclics, serotonin norepinephrine reuptake inhibitors, norepinephrine reuptake inhibitors, norepinephrine and dopamine reuptake inhibitors, and combinations thereof.

10. The method of claim 9, wherein the antidepressants are selected from the group consisting of fluoxetine, paroxetine, citalopram, escitalopram, fluvoxamine, sertraline, amitriptyline, nortriptyline, desipramine, trazodone, venlafaxine, duloxetine, milnacipran, nefopam, bupropion, and combinations thereof.

11. The method of claim 4, wherein the one or more additional active agents are formulated in the same pharmaceutical composition with droxidopa.

12. The method of claim 4, wherein the one or more additional active agents are administered in a pharmaceutical composition separate from droxidopa.

13. The method of claim 1, comprising administering the droxidopa in combination with a DOPA decarboxylase inhibiting compound.

14. The method of claim 13, comprising administering the droxidopa in combination with carbidopa.

15. The method of claim 13, wherein the DOPA decarboxylase inhibiting compound is formulated in the same pharmaceutical composition with the droxidopa.

16. The method of claim 13, wherein the DOPA decarboxylase inhibiting compound is administered in a pharmaceutical composition separate from the droxidopa.

17. The method of claim 1, wherein the droxidopa is administered once daily.

18. The method of claim 1, wherein the droxidopa is administered twice daily.

19. The method of claim 1, wherein the droxidopa is administered three times daily.

20. The method of claim 1, wherein the droxidopa is administered as a sustained-release composition.

* * * * *